(12) United States Patent
Doi

(10) Patent No.: US 8,248,465 B2
(45) Date of Patent: Aug. 21, 2012

(54) MEASURING ENDOSCOPE APPARATUS AND PROGRAM

(75) Inventor: Takahiro Doi, Tokyo (JP)

(73) Assignee: Olympus Corporation, Tokyo (JP)

( * ) Notice: Subject to any disclaimer, the term of this patent is extended or adjusted under 35 U.S.C. 154(b) by 760 days.

(21) Appl. No.: 12/340,891

(22) Filed: Dec. 22, 2008

(65) Prior Publication Data

US 2009/0167847 A1 Jul. 2, 2009

(30) Foreign Application Priority Data

Dec. 27, 2007 (JP) ................................ P2007-338002
Oct. 31, 2008 (JP) ................................ P2008-281474

(51) Int. Cl.
*A62B 1/04* (2006.01)

(52) U.S. Cl. ............. 348/65; 348/68; 348/70; 600/160; 600/168; 600/176

(58) Field of Classification Search .................... 348/65, 348/68, 69, 70, 71; 601/101, 109, 137, 160, 601/168, 176
See application file for complete search history.

(56) References Cited

U.S. PATENT DOCUMENTS

| | | | |
|---|---|---|---|
| 7,048,685 B2 * | 5/2006 | Sakiyama | 600/175 |
| 7,564,626 B2 * | 7/2009 | Bendall et al. | 359/462 |
| 7,850,598 B2 * | 12/2010 | Kobayashi et al. | 600/109 |
| 2002/0137986 A1 * | 9/2002 | Ogawa | 600/160 |
| 2002/0191074 A1 * | 12/2002 | Ogawa | 348/65 |
| 2004/0019255 A1 * | 1/2004 | Sakiyama | 600/175 |
| 2006/0176321 A1 | 8/2006 | Nakano et al. | |
| 2006/0249737 A1 * | 11/2006 | Fujimori | 257/79 |
| 2006/0268257 A1 * | 11/2006 | Ogawa | 356/3.13 |
| 2007/0177153 A1 * | 8/2007 | Takahashi | 356/479 |
| 2007/0291246 A1 * | 12/2007 | Oishi | 355/67 |

FOREIGN PATENT DOCUMENTS

| | | |
|---|---|---|
| JP | 2006-015117 A | 1/2006 |
| JP | 2006-325741 A | 12/2006 |

* cited by examiner

*Primary Examiner* — Lashonda Jacobs
(74) *Attorney, Agent, or Firm* — Holtz, Holtz, Goodman & Chick, PC

(57) ABSTRACT

A measuring endoscope apparatus includes: an endoscope that performs photoelectric conversion of a subject image to generate an imaging signal; an imaging signal processing unit that processes the imaging signal to generate image data; a measurement unit that executes measurement based on a principle of triangulation using the image data; a display signal generating unit that generates a display signal for displaying a measurement result; a determination unit that determines the reliability of the measurement result on the basis of the image data; and a control unit that executes a control according to a determination result.

24 Claims, 24 Drawing Sheets

MEASURING ENDOSCOPE APPARATUS AND PROGRAM

BACKGROUND OF THE INVENTION

1. Field of the Invention

The present invention relates to a measuring endoscope apparatus that performs measurement based on the principle of triangulation using image data, and a program for controlling the operation.

Priority is claimed on Japanese Patent Application No. 2007-338002 filed on Dec. 27, 2007, and Japanese Patent Application No. 2008-281474 filed on Oct. 31, 2008, the contents of which are incorporated herein by reference.

2. Description of Related Art

Industrial endoscopes are used to observe or check inside damage or corrosion of boilers, turbines, engines, chemical plants, water pipes, and the like. Industrial endoscopes have a plurality of kinds of optical adapters to observe and check various objects, and tip portions of the industrial endoscopes can be replaced.

An example of such an optical adapter includes a stereo optical adapter which forms two left and right fields of view in an observation optical system. Japanese unexamined Patent Application, First Publication No. 2006-15117 discloses a measuring endoscope apparatus that uses a stereo optical adapter, calculates the three-dimensional spatial coordinates of a subject on the basis of the coordinates of left and right optical system distance measurement points when a subject image is captured by left and right optical systems using the principle of triangulation, and measures a distance between two points on the subject. In addition, Japanese unexamined Patent Application, First Publication No. 2006-325741 discloses a measuring endoscope apparatus that calculates the three-dimensional spatial coordinates of a subject at high speed by similarly using the principle of triangulation, and measures a distance (object distance) to the subject in real time.

FIGS. 24 and 25 show screens (hereinafter, referred to as "display screens") displayed by a display device of a measuring endoscope apparatus. FIG. 24 shows a display screen in measuring a distance between two points, and FIG. 25 shows a display screen in measuring an object distance. A left image 2410 and a right image 2420 corresponding to left and right subject images captured by an optical adapter are displayed on a display screen 2400 shown in FIG. 24. Similarly, a left image 2510 and a right image 2520 are displayed on a display screen 2500 shown in FIG. 25.

As shown in FIG. 24, when a user designates measurement points 2440a and 2440b on a subject 2430 of the left image 2410, matching processing for calculating the positions of corresponding points 2450a and 2450b on the right image 2420, which correspond to the measurement points 2440a and 2440b, by image pattern matching is performed. Then, three-dimensional coordinates of a first point on the subject corresponding to the measurement point 2440a are calculated from two-dimensional coordinates of the measurement point 2440a and its corresponding point 2450a and optical data. Similarly, three-dimensional coordinates of a second point on the subject corresponding to the measurement point 2440b are calculated from two-dimensional coordinates of the measurement point 2440b and its corresponding point 2450b and optical data. A distance between the two points is calculated from the three-dimensional coordinates of the first and second points and is displayed as a measurement result 2460.

In addition, as shown in FIG. 25, when the user designates a measurement point 2540 on a subject 2530 of the left image 2510, the position of a corresponding point 2550 on the right image 2520, which corresponds to the measurement point 2540, is calculated by matching processing. Then, three-dimensional coordinates of a point on the subject corresponding to the measurement point 2540 are calculated from two-dimensional coordinates of the measurement point 2540 and its corresponding point 2550 and optical data. An object distance is calculated from the three-dimensional coordinates of the point and is displayed as a measurement result 2560.

However, when the brightness of an image is not appropriate as in a case where an image used for measurement is too bright or too dark, when there is no characteristic pattern on an image, or when it is difficult to secure the measurement accuracy because a distance to a subject is too far, the matching processing often fails. For example, the matching processing on the measurement point 2440b failed in FIG. 24, and the matching processing on the measurement point 2540 failed in FIG. 25. As a result, erroneous measurement results were displayed.

The measurement may be performed again as long as it can be immediately checked that there is an error in the measurement results. However, if the user does not recognize that the measurement result is erroneous at a point of time when the measurement has been performed, and recognizes later that the measurement result is erroneous since the user did not check whether or not the point on the right image corresponding to the measurement point designated on the left image was correctly calculated by the matching processing, the measurement should be done again from the beginning, for example. As a result, working efficiency is lowered.

SUMMARY OF THE INVENTION

According to an aspect of the invention, there is provided a measuring endoscope apparatus including: an endoscope that performs photoelectric conversion of a subject image to generate an imaging signal; an imaging signal processing unit that processes the imaging signal to generate image data; a measurement unit that executes measurement based on a principle of triangulation using the image data; a display signal generating unit that generates a display signal for displaying a measurement result; a determination unit that determines the reliability of the measurement result on the basis of the image data; and a control unit that executes a control according to a determination result.

Furthermore, in the measuring endoscope apparatus according to the aspect of the invention, it is preferable that the control unit determine the reliability of the measurement result and control a display form of the measurement result according to the determination result.

Furthermore, in the measuring endoscope apparatus according to the aspect of the invention, it is preferable that the control unit control a display form of the measurement result according to a value of a distance from a measurement position on a subject to an imaging surface of the endoscope.

Furthermore, in the measuring endoscope apparatus according to the aspect of the invention, it is preferable that the control unit control a display form of the measurement result according to a value of a correlation function of a plurality of subject images regarding the same subject.

Furthermore, in the measuring endoscope apparatus according to the aspect of the invention, it is preferable that the control unit control a display form of the measurement result according to a contrast value of a texture of a plurality of subject images regarding the same subject.

Furthermore, in the measuring endoscope apparatus according to the aspect of the invention, it is preferable that the control unit control a display form of the measurement result according to a parallax of a corresponding point on another subject image corresponding to a measurement point on one subject image regarding the same subject from an epipolar line.

Furthermore, in the measuring endoscope apparatus according to the aspect of the invention, when it is determined that the reliability of the measurement result is low, the control unit preferably executes a control of changing to a modification mode in which a corresponding point on another subject image corresponding to a measurement point on a subject image regarding the same subject is modified.

Furthermore, in the measuring endoscope apparatus according to the aspect of the invention, preferably, the measurement unit executes the measurement on the basis of a measurement point on a first subject image and a corresponding point on a second subject image corresponding to the measurement point, and the control unit executes a control of displaying the measurement result earlier than displaying a region including the corresponding point when it is determined that the reliability of the measurement result is low.

Furthermore, in the measuring endoscope apparatus according to the aspect of the invention, it is preferable that the determination unit determine the reliability of the measurement result on the basis of the image data before the measurement unit executes the measurement.

Furthermore, in the measuring endoscope apparatus according to the aspect of the invention, it is preferable that the determination unit determine the reliability of the measurement result on the basis of the image data after the measurement unit executes the measurement.

Furthermore, in the measuring endoscope apparatus according to the aspect of the invention, it is preferable that the determination unit execute first determination processing for determining the reliability of the measurement result on the basis of the image data before the measurement unit executes the measurement, and execute second determination processing for determining the reliability of the measurement result on the basis of the image data after the measurement unit executes the measurement.

Furthermore, it is preferable that the measuring endoscope apparatus according to the aspect of the invention further include an input unit to which an instruction to move a pointer indicating a position of a measurement point on the subject image and an instruction to start the measurement are input. In addition, preferably, the display signal generating unit generates a display signal for displaying an image based on the image data, the measurement result, and the pointer, and the determination unit determines the reliability of the measurement result at the position of the measurement point until the instruction to start the measurement is input to the input unit after the instruction to move the pointer is input to the input unit.

Furthermore, in the measuring endoscope apparatus according to the aspect of the invention, preferably, the display signal generating unit generates a display signal for displaying an image based on the image data and the measurement result, and the control unit executes a control of displaying the determination result outside a measurable region on the image.

In addition, according to another aspect of the invention, there is provided program causing a measuring endoscope apparatus to function as: an endoscope that performs photo-electric conversion of a subject image to generate an imaging signal; an imaging signal processing unit that processes the imaging signal to generate image data; a measurement unit that executes measurement based on a principle of triangulation using the image data; a display signal generating unit that generates a display signal for displaying a measurement result; a determination unit that determines the reliability of the measurement result on the basis of the image data; and a control unit that executes a control according to a determination result.

Furthermore, in the program according to the aspect of the invention, preferably, the measurement unit executes the measurement on the basis of a measurement point on a first subject image and a corresponding point on a second subject image corresponding to the measurement point, and the control unit executes a control of displaying the measurement result earlier than displaying a region including the corresponding point when it is determined that the reliability of the measurement result is low.

Furthermore, in the program according to the aspect of the invention, it is preferable that the determination unit determine the reliability of the measurement result on the basis of the image data before the measurement unit executes the measurement.

Furthermore, in the program according to the aspect of the invention, it is preferable that the determination unit determine the reliability of the measurement result on the basis of the image data after the measurement unit executes the measurement.

Furthermore, in the program according to the aspect of the invention, it is preferable that the determination unit execute first determination processing for determining the reliability of the measurement result on the basis of the image data before the measurement unit executes the measurement, and execute second determination processing for determining the reliability of the measurement result on the basis of the image data after the measurement unit executes the measurement.

Furthermore, it is preferable that the program according to the aspect of the invention cause the measuring endoscope apparatus to further function as an input unit to which an instruction to move a pointer indicating a position of a measurement point on the subject image and an instruction to start the measurement are input. In addition, preferably, the display signal generating unit generates a display signal for displaying an image based on the image data, the measurement result, and the pointer, and the determination unit determines the reliability of the measurement result at the position of the measurement point until the instruction to start the measurement is input to the input unit after the instruction to move the pointer is input to the input unit.

Furthermore, in the program according to the aspect of the invention, preferably, the display signal generating unit generates a display signal for displaying an image based on the image data and the measurement result, and the control unit executes a control of displaying the determination result outside a measurable region on the image.

DETAILED DESCRIPTION OF THE INVENTION

Figure 1:
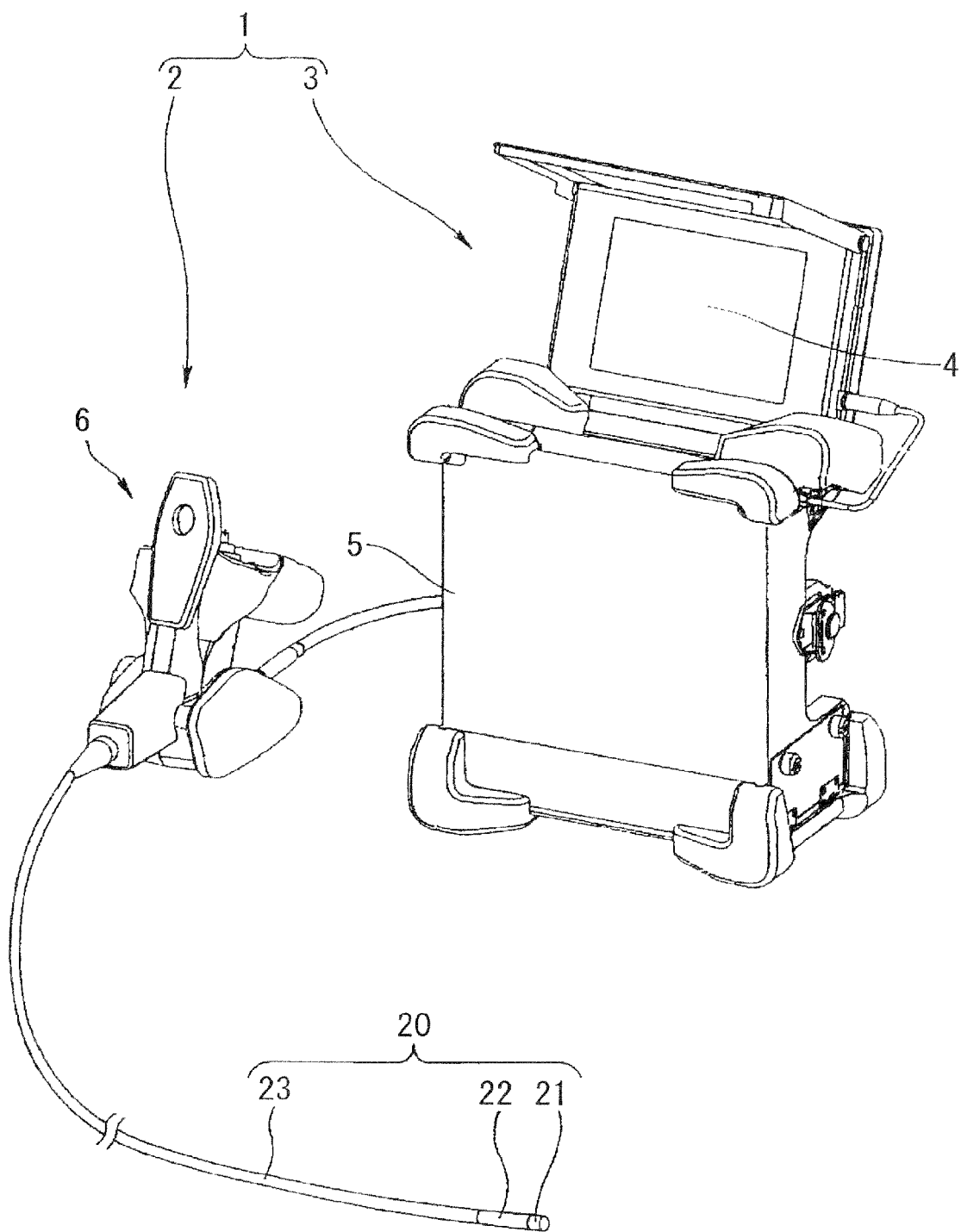
FIG. 1 is a perspective view illustrating the entire configuration of a measuring endoscope apparatus according to an embodiment of the invention.

Hereinafter, embodiments of the invention will be described with reference to the accompanying drawings. FIG. 1 shows the entire configuration of a measuring endoscope apparatus according to an embodiment of the invention. As shown in FIG. 1, a measuring endoscope apparatus 1 includes an endoscope 2 and a main apparatus body 3 connected to the endoscope 2. The endoscope 2 includes an elongated insertion portion 20 and an operating portion 6 for performing an operation required in executing various kinds of operation controls of the entire apparatus. The main apparatus body 3 includes a monitor 4 (liquid crystal monitor), which is a display device that displays an image of a subject imaged by the endoscope 2, details of an operation control (for example, a processing menu), and the like, and a housing 5 having a control unit 10 (refer to FIG. 2) therein.

The insertion portion 20 is formed by connecting a hard tip portion 21a curved portion 22 which can be curved, for example, in the upper, lower, left, and right directions, and a flexible tube portion 23 with the flexibility sequentially from the tip side. Various kinds of optical adapters, such as a stereo optical adapter having two observation fields of view or a normal observation optical adapter having one observation field of view, are freely attached to the tip portion 21 or detached from the tip portion 21.

Figure 2:
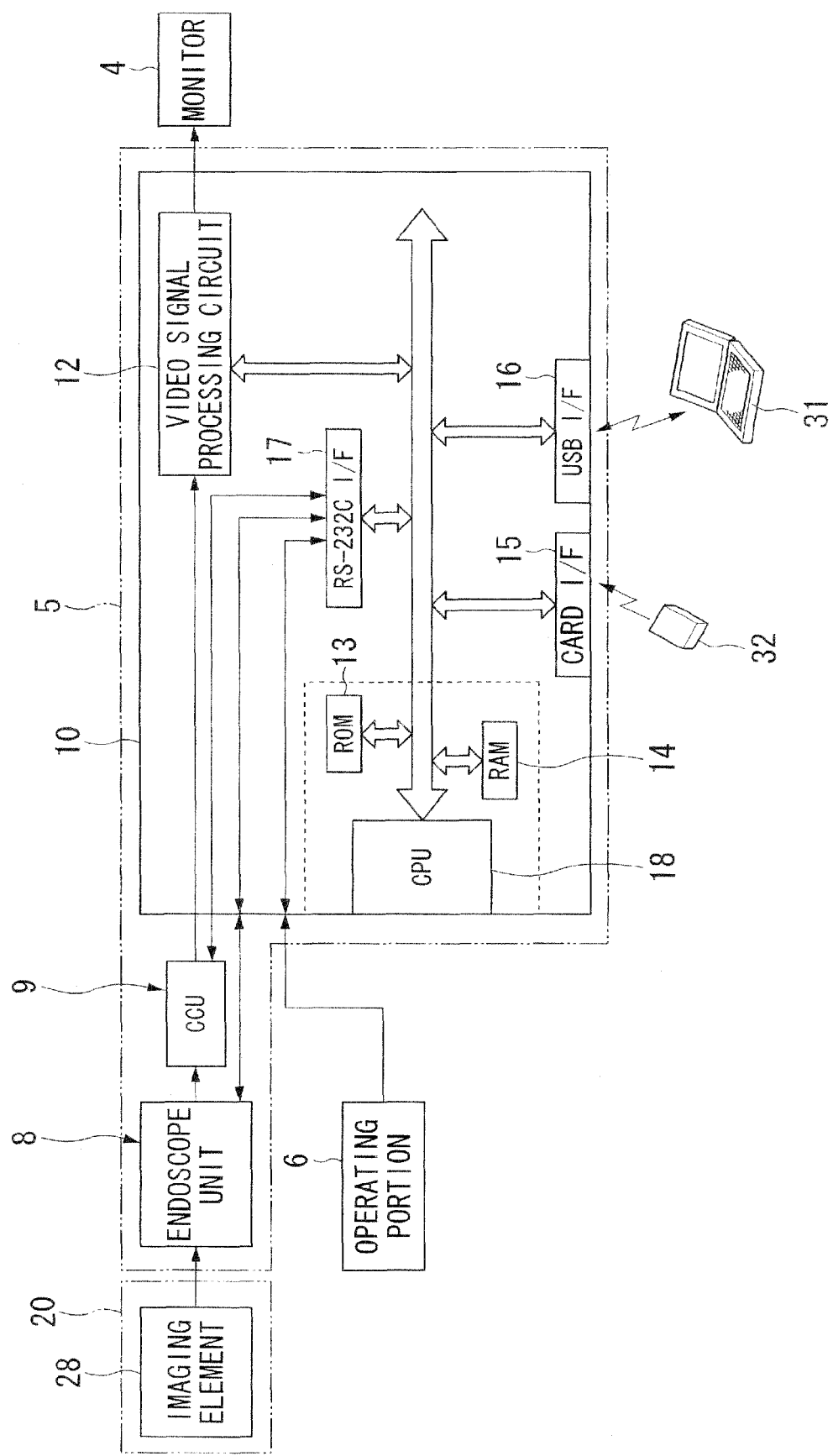
FIG. 2 is a block diagram illustrating the internal configuration of a measuring endoscope apparatus according to an embodiment of the invention.

As shown in FIG. 2, an endoscope unit 8, CCU 9 (camera control unit), and a control unit 10 are provided in the housing 5. A base end portion of the insertion portion 20 is connected to the endoscope unit 8. The endoscope unit 8 is configured to include a light source (not shown) which supplies illumination light required at the time of observation and a curving device (not shown) which curves the curved portion 22 provided in the insertion portion 20.

An imaging device 28 is provided in the tip portion 21 of the insertion portion 20. The imaging device 28 generates an imaging signal by performing photoelectric conversion of a subject image formed through the optical adapter. The imaging signal output from the imaging device 28 is input to the CCU 9. The imaging signal is converted into a video signal (image data), such as an NTSC signal, in the CCU 9 and is then supplied to the control unit 10.

A video signal processing circuit 12 to which a video signal is input, a ROM 13, a RAM 14, a card I/F 15 (card interface), a USB I/F 16 (USB interface), an RS-232C I/F 17 (RS-232C interface), and a CPU 18 that executes these various functions on the basis of a main program and performs various controls are provided in the control unit 10.

The CCU 9 and the endoscope unit 8 are connected to the RS-232C I/F 17. In addition, the operating portion 6 which performs control and operation instructions of the CCU 9, endoscope unit 8, and the like is connected to the RS-232C I/F 17. When a user operates the operating portion 6, a communication required in controlling the CCU 9 and the endoscope unit 8 is performed on the basis of the operation.

The USB I/F 16 is an interface for electrically connecting the control unit 10 and a personal computer 31 with each other. By connecting the control unit 10 with the personal computer 31 through the USB I/F 16, various kinds of instruction controls, such as an instruction to display an endoscope image or image processing at the time of measurement can be performed at the side of the personal computer 31. In addition, input and output of control information, data, or the like which are required for various kinds of processing, between the control unit 10 and the personal computer 31 can also be performed.

In addition, a memory card 32 can be freely attached to the card I/F 15 or detached from the card I/F 15. By mounting the memory card 32 in the card I/F 15, capturing of data such as control processing information or image information stored in the memory card 32 into the control unit 10 or recording of data such as control processing information or image information into the memory card 32 can be performed according to the control of the CPU 18.

In order to display a synthetic image obtained by synthesizing an endoscope image supplied from the CCU 9 with an operation menu using a graphic, the video signal processing circuit 12 performs processing for synthesizing an a graphic image signal based on the operation menu, which is generated by the control of the CPU 18, with the video signal from the CCU 9, processing required for display on the screen of the monitor 4, and the like and supplies a display signal to the monitor 4. In addition, the video signal processing circuit 12 may also perform processing for simply displaying an endoscope image or an image, such as an operation menu, independently. Accordingly, the endoscope image, the operation menu image, or the synthetic image obtained by synthesizing the endoscope image with the operation menu image or the like is displayed on the screen of the monitor 4.

The CPU 18 controls an operation of the entire measuring endoscope apparatus 1 by executing a program stored in the ROM 13 in order to control various circuit portions to perform processing corresponding to the purpose. The CPU 18 uses the RAM 14 as a working area for temporarily storing data.

Figure 3:
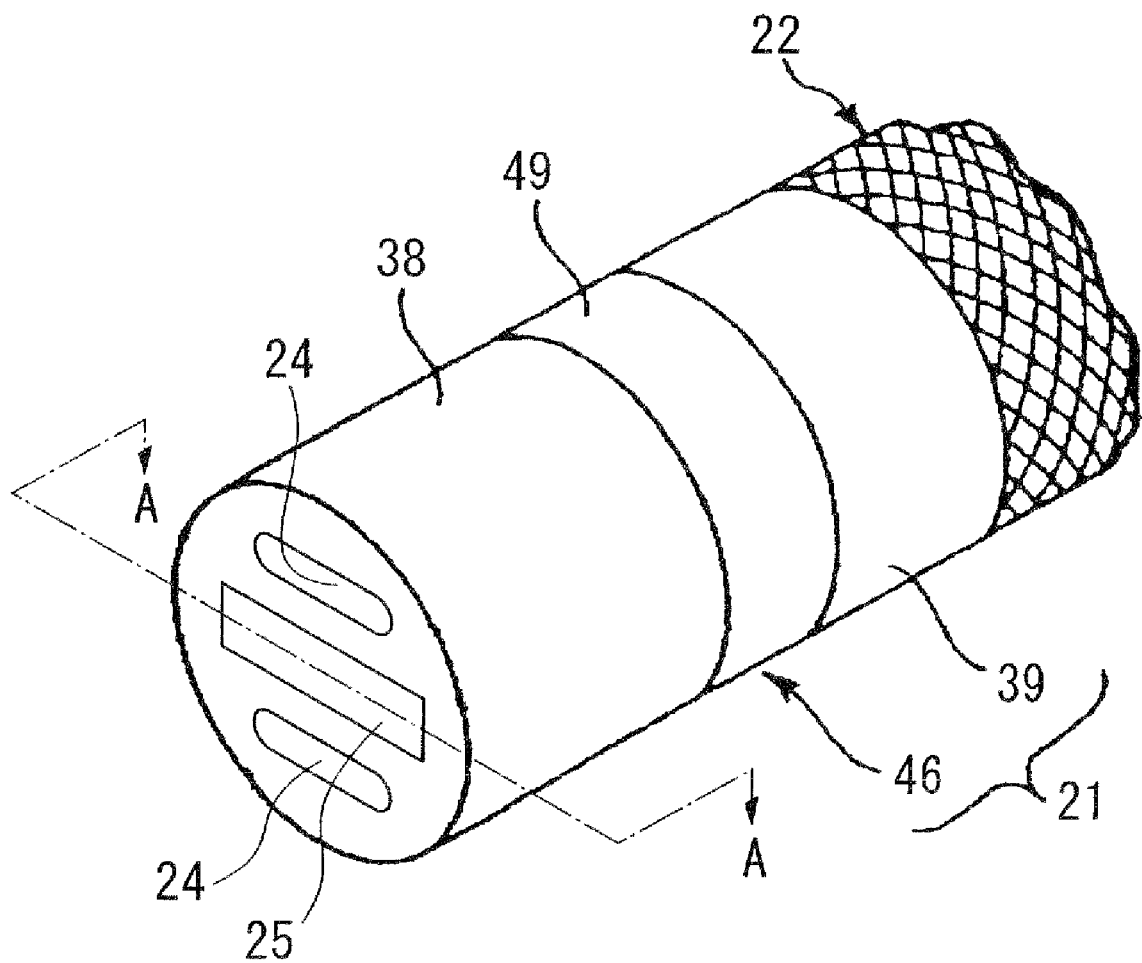
FIG. 3 is a perspective view illustrating a tip portion of an insertion portion of an endoscope provided in a measuring endoscope apparatus according to an embodiment of the invention.
Figure 4:
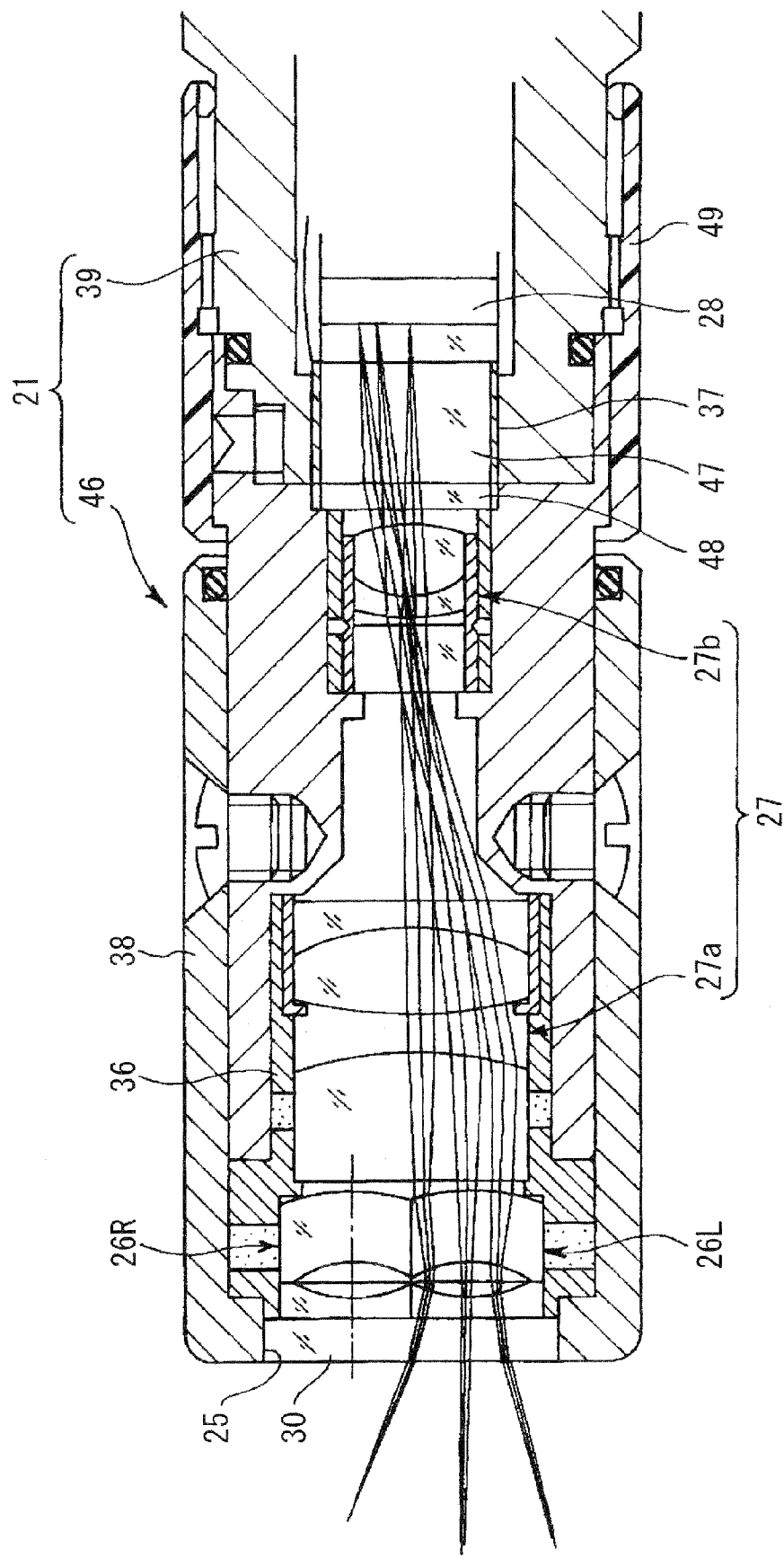
FIG. 4 is a cross-sectional view illustrating a tip portion of an insertion portion of an endoscope provided in a measuring endoscope apparatus according to an embodiment of the invention.

FIG. 3 is a perspective view illustrating the tip portion 21 of the insertion portion 20 provided in the endoscope 2, and FIG. 4 is a cross-sectional view taken along the line A-A of FIG. 3. As shown in FIG. 3, the tip portion 21 is configured to include a tip portion body 39 and an optical adapter 46 which can be freely attached to the tip portion body 39 or detached from the tip portion body 39. Two illuminators 24 formed of LEDs, for example, and an observation window 25 for capturing a subject image are provided on a tip surface of the tip portion 21. As shown in FIG. 4, the observation window 25 provided in the tip portion body 39 of the tip portion 21 is blocked with a cover glass 30. In addition, a pair of objective optical systems, that is, an objective optical system 26R for a right image and an objective optical system 26L for a left image are attached to the inside through a lens frame 36.

The lens frame 36 extends rearward, and a previous-stage-side optical system 27a of a common image transmission optical system 27 is attached to the lens frame 36. In addition, the imaging device 28 is fixed to an imaging device fixing frame 37 housed in a hole at a rear end side of the lens frame 36. A later-stage-side optical system 27b of the image transmission optical system 27 is attached to a front portion side of an imaging surface of the imaging device 28 through a lens frame. In addition, the outer periphery at the front end side of the tip portion body 39 is covered with a cylindrical cover member 38, and this cover member 38 is fixed to the tip portion body 39 with a screw. In addition, an O ring for sealing is inserted between the cover member 38 and the tip portion body 39, such that a watertight construction is formed.

Images obtained by the objective optical system 26R and the objective optical system 26L are formed at different left and right positions on the imaging device 28 through the image transmission optical system 27. That is, a right imaging optical system, which is an optical system using the objective optical system 26R and the image transmission optical system 27, and a left imaging optical system, which is an optical system using the objective optical system 26L and the image transmission optical system 27, are formed. An imaging signal photoelectrically converted by the imaging device 28 is supplied to the CCU 9 through the endoscope unit 8 and is converted into a video signal. Then, the video signal is supplied to the video signal processing circuit 12.

In addition, the front surface side of the imaging device 28 is protected by a cover glass 47, and the cover glass 47 faces a cover glass 48 on a side of the optical adapter 46. A fixing ring 49 is provided on an outer peripheral surface at the rear end side of the optical adapter 46 such that the optical adapter 46 can be freely attached or detached by screwing a male screw portion, which is provided on the outer peripheral surface of the tip portion body 39, to a female screw portion provided on an inner peripheral surface of the endoscope at the rear end of the fixing ring 49. A positioning recess is provided on the outer peripheral surface of a tip surface of the tip portion body 39 and a positioning pin is provided on the optical adapter 46, such that positioning in the peripheral direction is performed by the recess and the pin when the optical adapter 46 is attached.

Next, a measurement method using the measuring endoscope apparatus 1 will be described. In a production process, optical data unique to each optical adapter 46 which is shown in the following (a1) to (e) is measured for every individual optical adapter 46. The optical data is recorded, for example, in a memory card which is a recording medium. The optical data recorded in the memory card corresponds to the characteristic of the optical adapter 46 in a one-to-one manner, and the optical data and the characteristic are treated as one combination after release. The optical data in the present embodiment is as follows. In addition, since details of optical data are disclosed in Japanese unexamined Patent Application, First Publication No. 2004-49638, for example, an explanation thereof will be omitted.

Figure 5:
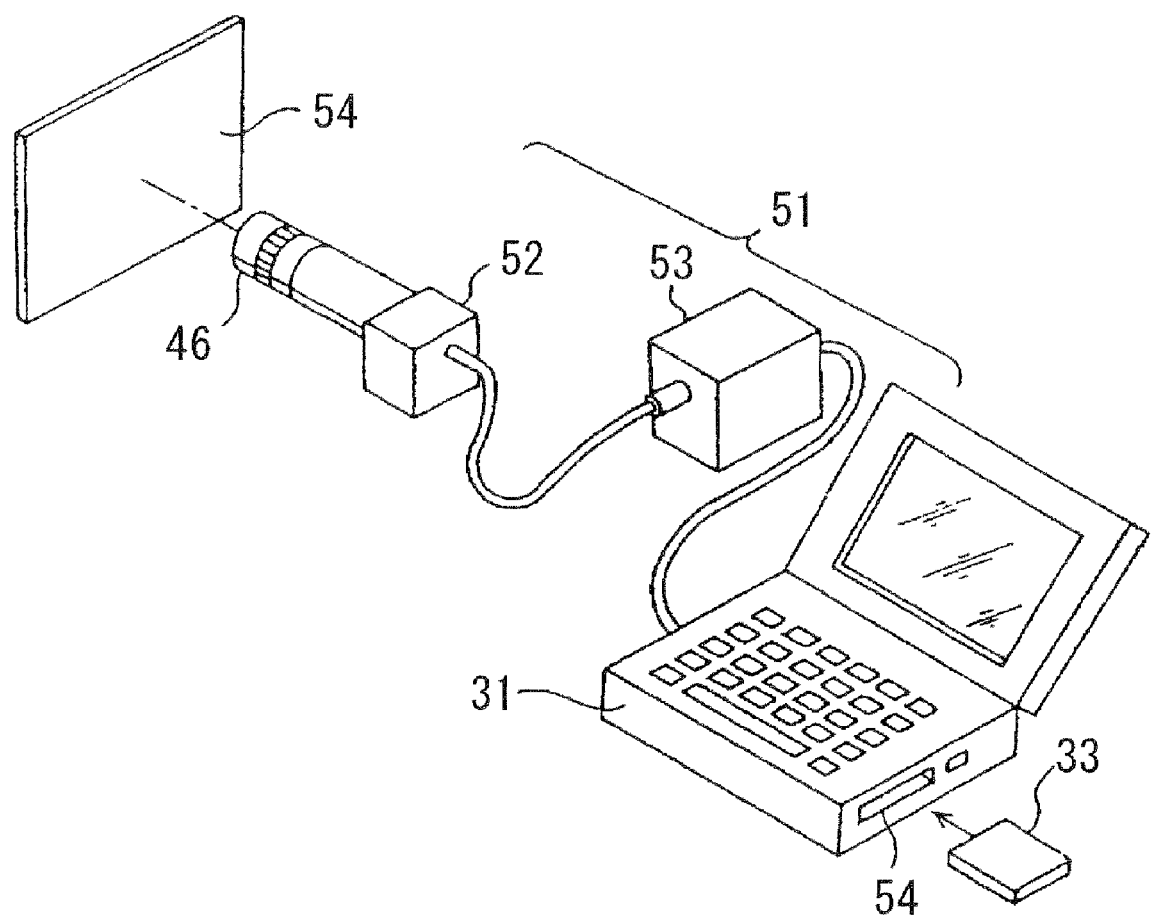
FIG. 5 is a perspective view illustrating how to measure optical data unique to an optical adapter applied to a measuring endoscope apparatus according to an embodiment of the invention.

(a1) Geometric distortion compensation table of two objective optical systems (a2) Geometric distortion compensation table of an image transmission optical system (b) A focal distance of each of left and right imaging optical systems (c) A distance between main points of left and right imaging optical systems (d) Optical axis position coordinates on an image of each of left and right imaging optical systems (e) Positional information when an image of each of left and right imaging optical systems is formed on a master imaging device Hereinafter, a method of measuring optical data will be described with reference to FIG. 5. A production measurement jig 51 which can be mounted with the optical adapter 46 is configured to include a master imaging unit 52, a CCU 53, a personal computer 31, and a chart 54.

The master imaging unit 52 has the same structure as the tip portion body 39 of the endoscope 2. The CCU 53 is connected to the master imaging unit 52 with a signal line. The personal computer 31 has a memory card slot 54 to which a memory card 33 can be attached or from which a memory card 33 can be detached and performs image processing on image data from the CCU 53. The chart 54 has a lattice-shaped pattern for analyzing the optical properties of the optical adapter 46.

When capturing optical data using the production measurement jig 51, first, the optical adapter 46 is attached to the master imaging unit 52, an image of the chart 54 is captured through the optical adapter 46, image processing is performed on the basis of the image data by the personal computer 31 to thereby obtain the optical data of (a1) to (e), and the optical data is recorded in the memory card 33, as shown in FIG. 5.

Various size measurements (stereo measurement) can be performed by attaching the optical adapter 46 after collecting the unique optical data to the endoscope 2 and performing processing of (1) to (8) shown below in the measuring endoscope apparatus 1. In addition, since details of the stereo measurement are disclosed in Japanese unexamined Patent Application, First Publication No. 2004-49638, for example, an explanation thereof will be omitted.

(1) Optical data of (a1) to (e) is read from the memory card 33

(2) A white subject is imaged by using the measuring endoscope apparatus 1

(3) Deviation of an image position caused by combination of the optical adapter 46 and the endoscope 2 is calculated by using the data of (e) and the imaging data of (2)

(4) A conversion table for performing geometric distortion correction on the endoscope 2 by using the data of (3) and the data of (1)

(5) An object to be measured which is a subject is imaged by the endoscope 2 and the image is captured (6) The captured image is subjected to coordinate transformation on the basis of the table generated in (3)

(7) Three-dimensional coordinates of an arbitrary point are calculated by matching of the imaging data of (2) on the basis of the image subjected to the coordinate transformation (8) Various size measurements are performed on the basis of the three-dimensional coordinates

FIRST OPERATION EXAMPLE

Figure 6:
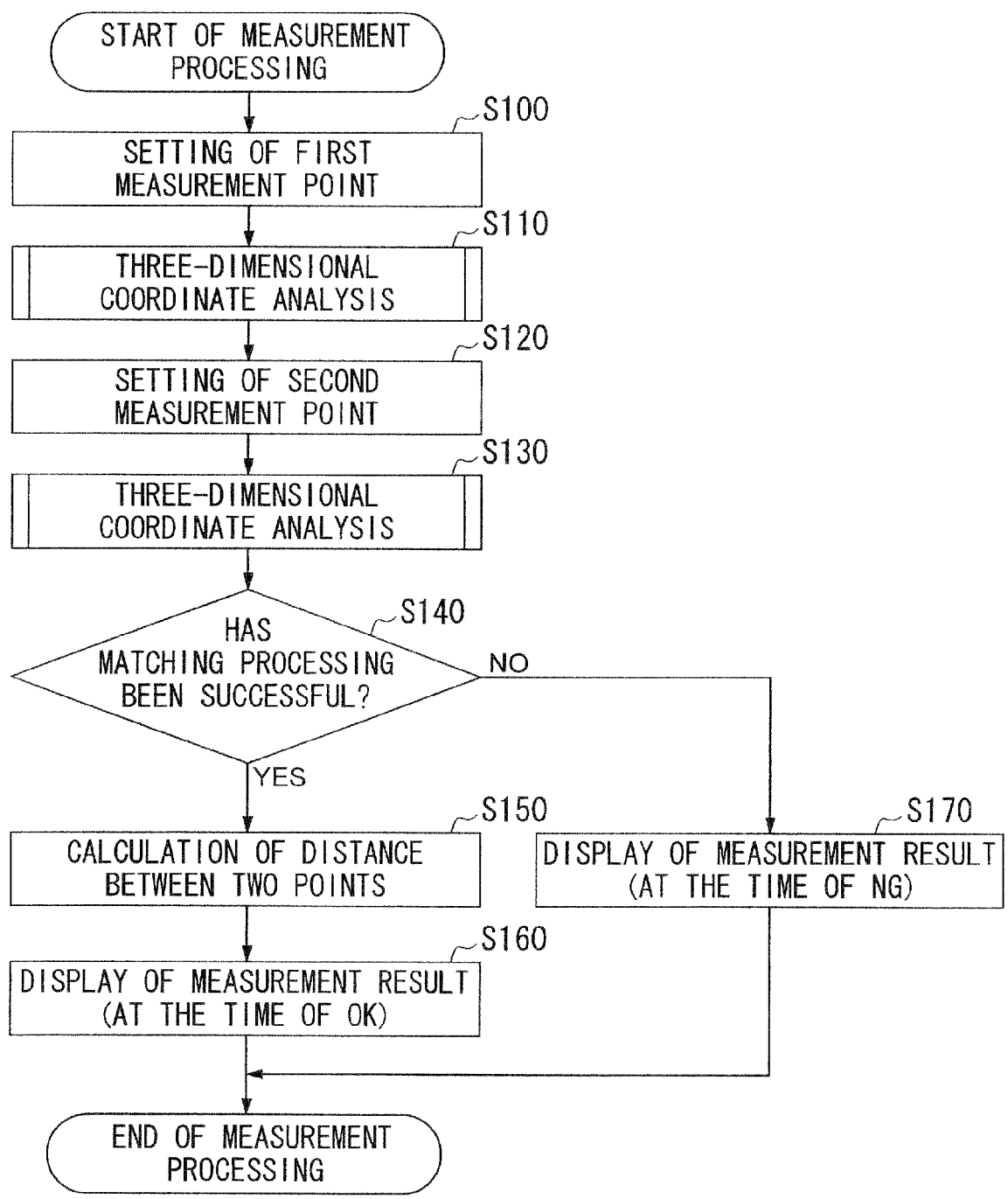
FIG. 6 is a flow chart illustrating the procedure of measurement processing (first operation example) executed by a measuring endoscope apparatus according to an embodiment of the invention.

Next, as a first operation example of measurement processing, an operation in measuring a distance between two points will be described. As shown in FIG. 6, a first measurement point is first set (step S100). At this time, a user inputs the first measurement point on a subject by operating the operating portion 6 while viewing a display screen of the monitor 4. The CPU 18 calculates the position (two-dimensional coordinates) of the first measurement point within an image on the basis of a signal output from the operating portion 6 and input to the CPU 18 through the RS-232C I/F 17. This is processing in step S100.

Then, the CPU 18 executes three-dimensional coordinate analysis processing and calculates the three-dimensional coordinates of the first measurement point (step S110). Details of the three-dimensional coordinate analysis processing will be described later. Then, in the same manner as described above, a second measurement point is set (step S120), and the three-dimensional coordinate analysis processing is executed to calculate the three-dimensional coordinates of the second measurement point (step S130).

Then, the CPU 18 determines whether or not matching processing has been successful on the basis of a value of a matching check flag (step S140). As described above, the matching processing refers to processing of calculating the position of a corresponding point (matching point) on a second subject image (for example, a right image) corresponding to the first measurement point designated on a first subject image (for example, a left image) regarding the same subject by image pattern matching. The matching processing is executed as a part of processing in steps S110 and S130. In addition, the matching check flag is a flag used for determination in step S140 related with the reliability of a measurement result and two kinds of flags, that is, a flag regarding the first measurement point and a flag regarding the second measurement point are used.

The value of the matching check flag is set to 0 or 1 in the three-dimensional coordinate analysis processing of steps S110 and S130, which will be described later. The matching processing is successful when the value of the matching check flag is 1, and the matching processing fails when the value of the matching check flag is 0.

When both values of two kinds of matching check flags are 1, it is determined that the matching processing executed as a part of steps S110 and S130 is successful at the same time, proceeding to step S150. In addition, when at least one value of the two kinds of matching check flags is 0, it is determined that at least one of the matching processing executed as a part of steps S110 and S130 has failed, proceeding to step S170.

When the matching processing executed as a part of steps S110 and S130 is successful at the same time, the CPU 18 calculates a distance between two points from the three-dimensional coordinates of the first and second measurement points (step S150). Then, the CPU 18 makes a control of displaying, as a measurement result, the distance between two points calculated in step S150 (step S160).

At this time, the CPU 18 generates a graphic image signal for displaying an operation menu or a measurement result and outputs the graphic image signal to the video signal processing circuit 12. The video signal processing circuit 12 synthesizes the graphic image signal with the video signal from the CCU 9, performs processing required for displaying a synthetic image on the screen of the monitor 4, and outputs a display signal to the monitor 4. The monitor 4 displays the synthetic image on the basis of the display signal. At this time, a measurement result of the distance between two points is displayed (for example, "L=2.00 mm"). This is processing in step S160.

On the other hand, when at least one of the matching processing executed as a part of steps S110 and S130 fails, the CPU 18 makes a control of displaying a failure of the matching processing as a measurement result (step S170). In this case, the control made by the CPU 18 is the same as in step S160 but a graphic image signal for displaying a measurement result is different. As a result, a display form of the measurement result in the synthetic image displayed on the monitor 4 is different from that when the matching processing is successful.

Figure 7A:
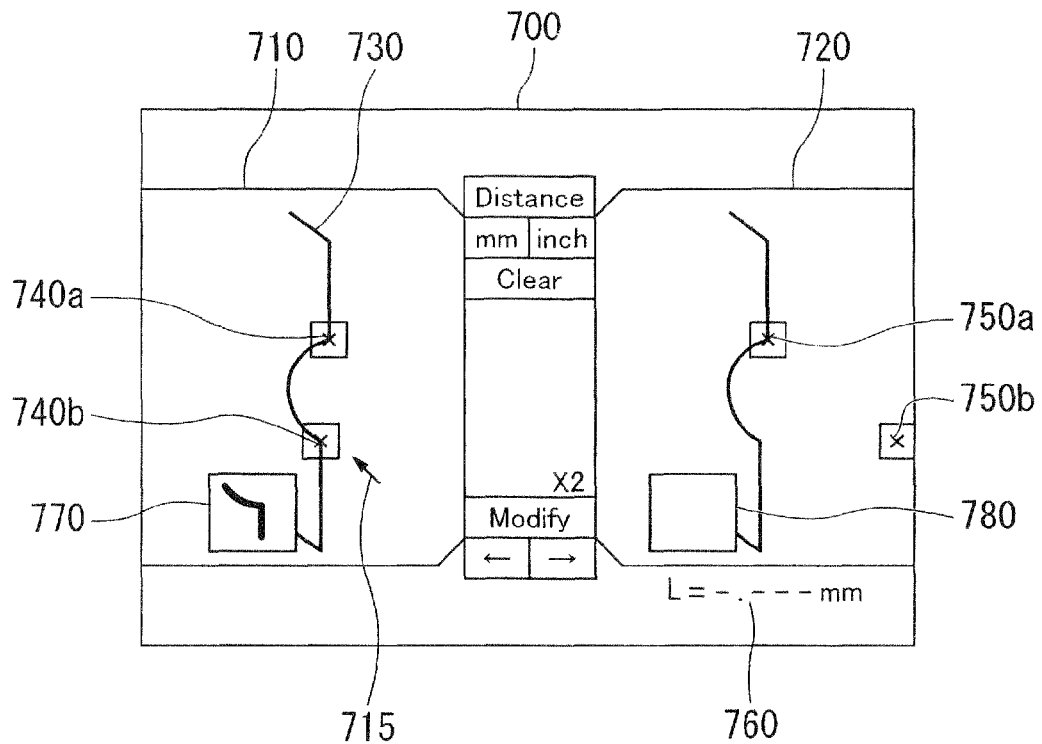
FIGS. 7A and 7B are reference views illustrating a display screen (first operation example) of a measuring endoscope apparatus according to an embodiment of the invention.
Figure 7B:
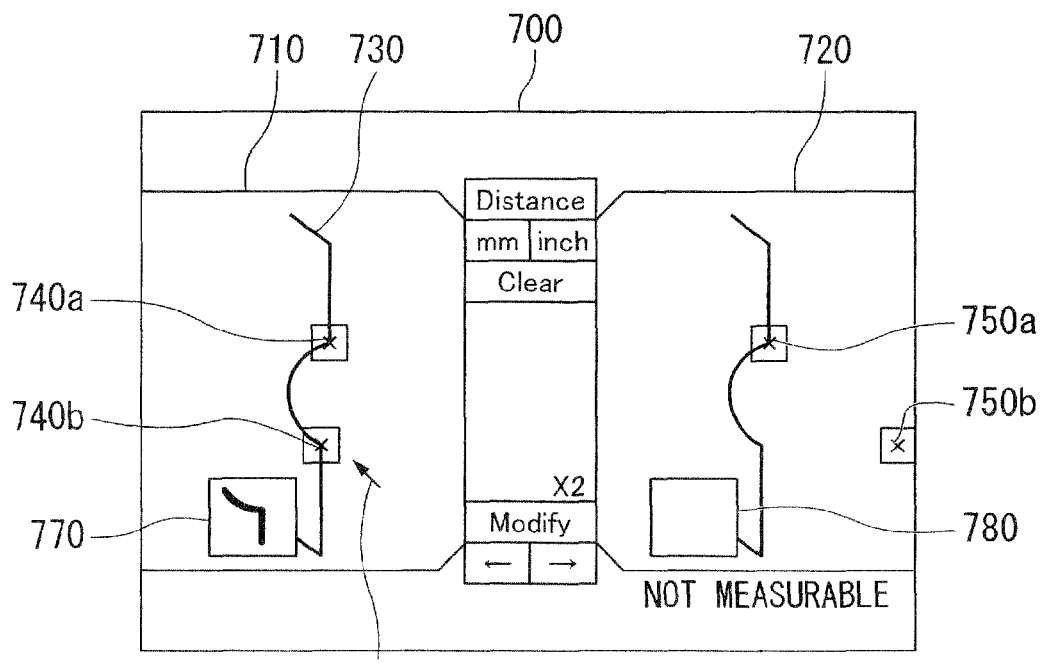

FIGS. 7A and 7B show display screens of the monitor 4. A left image 710 and a right image 720 corresponding to left and right subject images captured by the optical adapter 46 are displayed on a display screen 700 shown in FIGS. 7A and 7B. When a user moves a pointer 715 on the left image 710 to designate measurement points 740a and 740b on a subject 730, the positions of corresponding points 750a and 750b on the right image 720 corresponding to the measurement points are calculated by matching processing. For example, as shown in FIGS. 7A and 7B, when the calculation accuracy of the measurement point 750b is low, a measurement result 760 is displayed like "-.---" (FIG. 7A) or "not measurable" (FIG. 7B) indicating a failure of the matching processing.

Thus, when the matching processing has failed, the measurement result is displayed by a special character or symbol, a graph, or a message. Therefore, the user can understand that the matching processing has failed from the measurement result. Although the display position of the measurement result showing that the matching processing has failed may be different from the display position of the measurement result when the matching processing has been successful, it is preferable to set the same display position in order to inform the user that the matching processing has failed more reliably without confusing the user. In addition, in order to make an endoscope image easily viewed, it is preferable to display a measurement result outside the endoscope image. In particular, it is preferable to display the measurement result outside a measurable region (region where a measurement point can be set). In addition, by also keeping a measurement point on the right image displayed when the matching processing has failed, it becomes easy to check the cause of the failure of the matching processing.

An enlarged image at the position of the measurement point 740b is displayed in a zoom window 770 on the left image 710, and an enlarged image at the position of the corresponding point 750b is displayed in a zoom window 780 on the right image 720. The user can recognize that the matching processing has failed from the facts that the position of the measurement point 740b is different from the position of the corresponding point 750b and an image of the zoom window 770 is different from an image of the zoom window 780.

Figure 8:
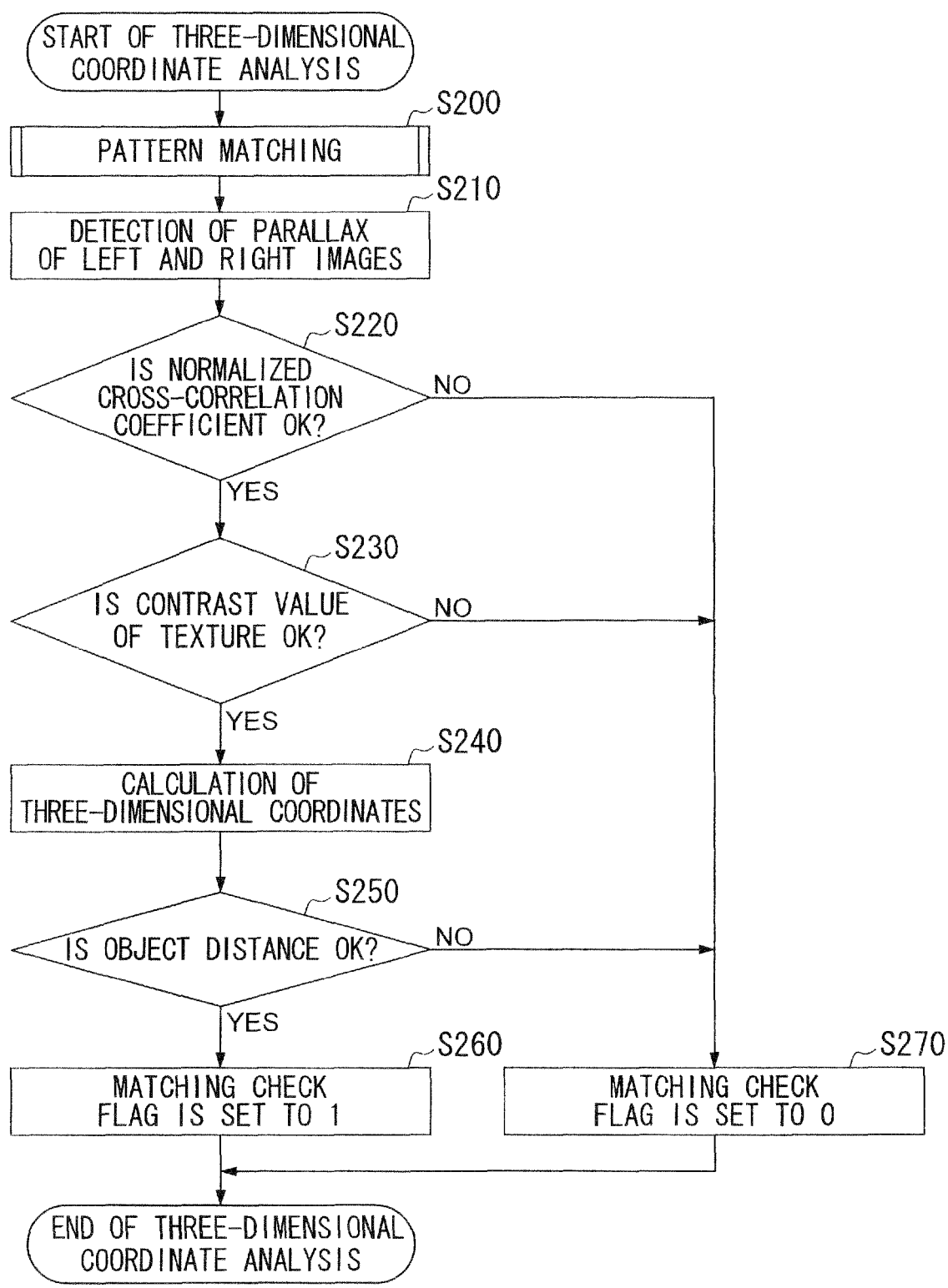
FIG. 8 is a flow chart illustrating the procedure of three-dimensional coordinate analysis processing (first operation example) executed by a measuring endoscope apparatus according to an embodiment of the invention.

Next, details of three-dimensional coordinate analysis processing in steps S110 and S130 (will be described. As shown in FIG. 8, first, the CPU 18 executes pattern matching processing to detect matching points which are corresponding points of two left and right images (stereo images) (step S200). Details of the pattern matching processing will be described later. Then, the CPU 18 calculates the amounts of deviation of the two left and right images from the coordinates of the corresponding points (step S210).

Then, the CPU 18 determines a value of a check flag regarding a normalized cross-correlation coefficient, which will be described later (step S220). The value of the check flag regarding the normalized cross-correlation coefficient is set by the pattern matching processing in step S200. When the value of the check flag regarding the normalized cross-correlation coefficient is 1, the process proceeds to step S230. When the value of the check flag regarding the normalized cross-correlation coefficient is 0, the process proceeds to step S270.

When the value of the check flag regarding the normalized cross-correlation coefficient is 1, the CPU 18 determines a value of a check flag regarding a contrast value of a texture (step S230). The value of the check flag regarding the contrast value of the texture is set by the pattern matching processing in step S200. When the value of the check flag regarding the contrast value of the texture is 1, the process proceeds to step S240. When the value of the check flag regarding the contrast value of the texture is 0, the process proceeds to step S270.

Figure 9:
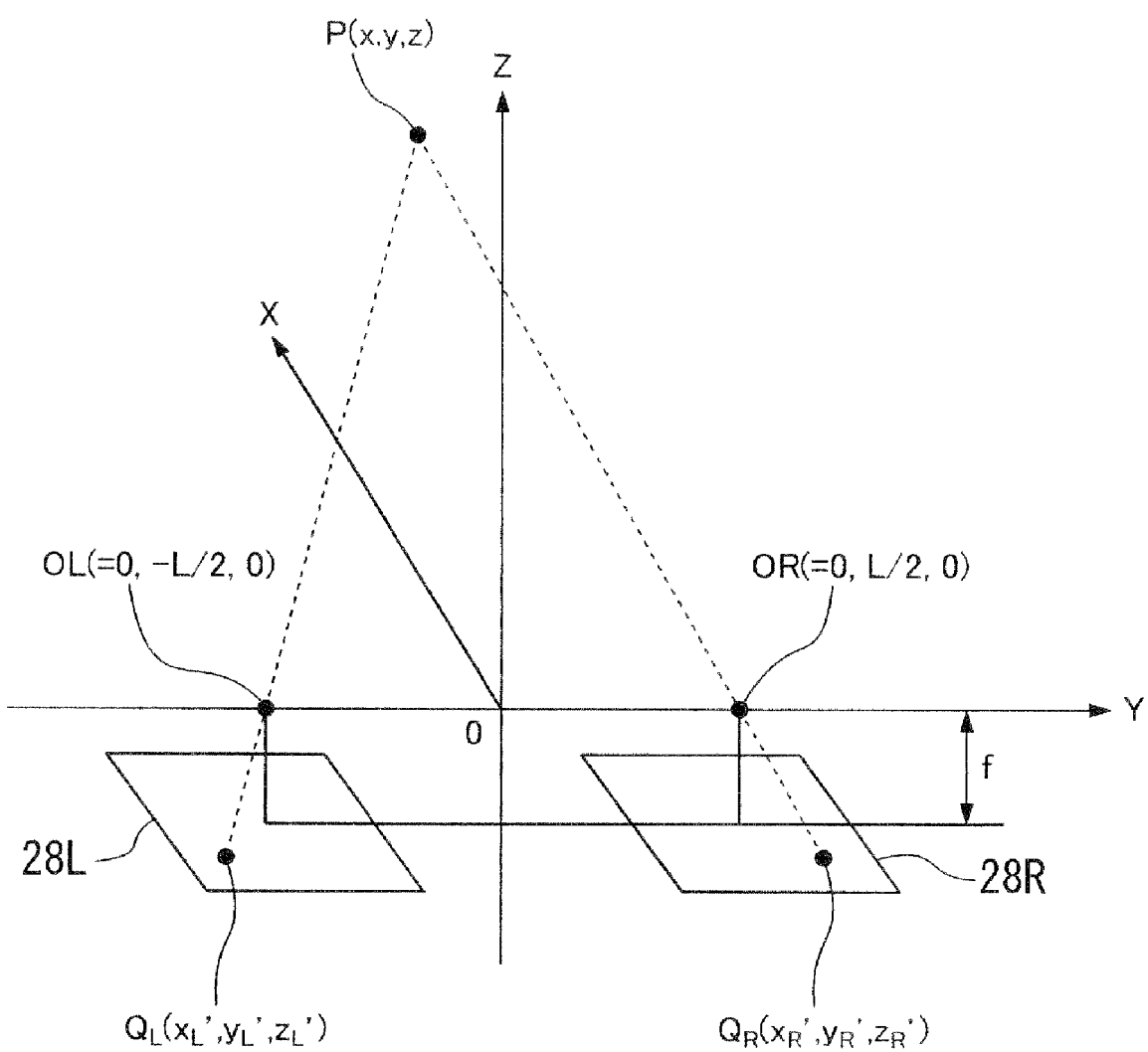
FIG. 9 is a reference view illustrating the basic principle of three-dimensional coordinate analysis in an embodiment of the invention.

When the value of the check flag regarding the contrast value of the texture is 1, the CPU 18 calculates the three-dimensional coordinates of a target point (step S240). Hereinafter, a basic principle of the three-dimensional coordinate analysis will be described using FIG. 9. FIG. 9 shows the positional relationship between two left and right images on a three-dimensional spatial coordinate system with x, y, and z axes. A state where a point P, a distance (object distance) of which to a subject is to be measured, is imaged on a right imaging surface 28R and a left imaging surface 28L of an imaging device is shown in FIG. 9. In FIG. 9, it is assumed that points OR and OL are main points of the optical system, a distance f is a focal length, points QR and QL are imaging positions of the point P, and a distance L, is the distance between the point OR and the point OL.

In FIG. 9, expression (1) is obtained from a straight line QR-OR.

$$x/xR = \{y-(L/2)\}/\{yR-(L/2)\} = z/(-f) \qquad (1)$$

In addition, expression (2) is obtained from a straight line QL-OL.

$$x/xL = \{y+(L/2)\}/\{yL+(L/2)\} = z/(-t) \qquad (2)$$

The three-dimensional coordinates of the point P are obtained by solving the expressions for x, y, and z. As a result, the distance (object distance) from the imaging surface of the endoscope 2 to the subject is calculated. In practice, since light beams of the two left and right images are curved by the effect of the image transmission optical system 27, the distance between the right imaging surface 28R and the left imaging surface 28L becomes smaller. However, the effect of the image transmission optical system 27 is omitted herein in order to make the drawing simple.

Subsequent to step S240, the CPU 18 determines a value of the object distance (step S250). When the value of the object distance is 0 or more, the process proceeds to step S260. When the value of the object distance is less than 0, the process proceeds to step S270. Although it is determined whether or not the object distance is 0 or more in the determination of step S250, the determination may be performed together with a result when a determination on whether or not the object distance is equal to or smaller than a predetermined value α (α>0) has been made. That is, when the object distance is 0 or more and α or less, the process proceeds to step S260. In other cases, the process proceeds to step S270.

When the value of the object distance is 0 or more, it can be seen that the matching processing is successful from the determination results in steps S220, S230, and S250 and therefore, the measurement result is reliable. In this case, the CPU 18 sets the value of the matching check flag to 1 (step S260). On the other hand, when the matching processing has failed from the determination results in steps S220, S230, and S250 and the measurement result is not reliable, the CPU 18 sets the value of the matching check flag to 0 (step S270).

Figure 10:
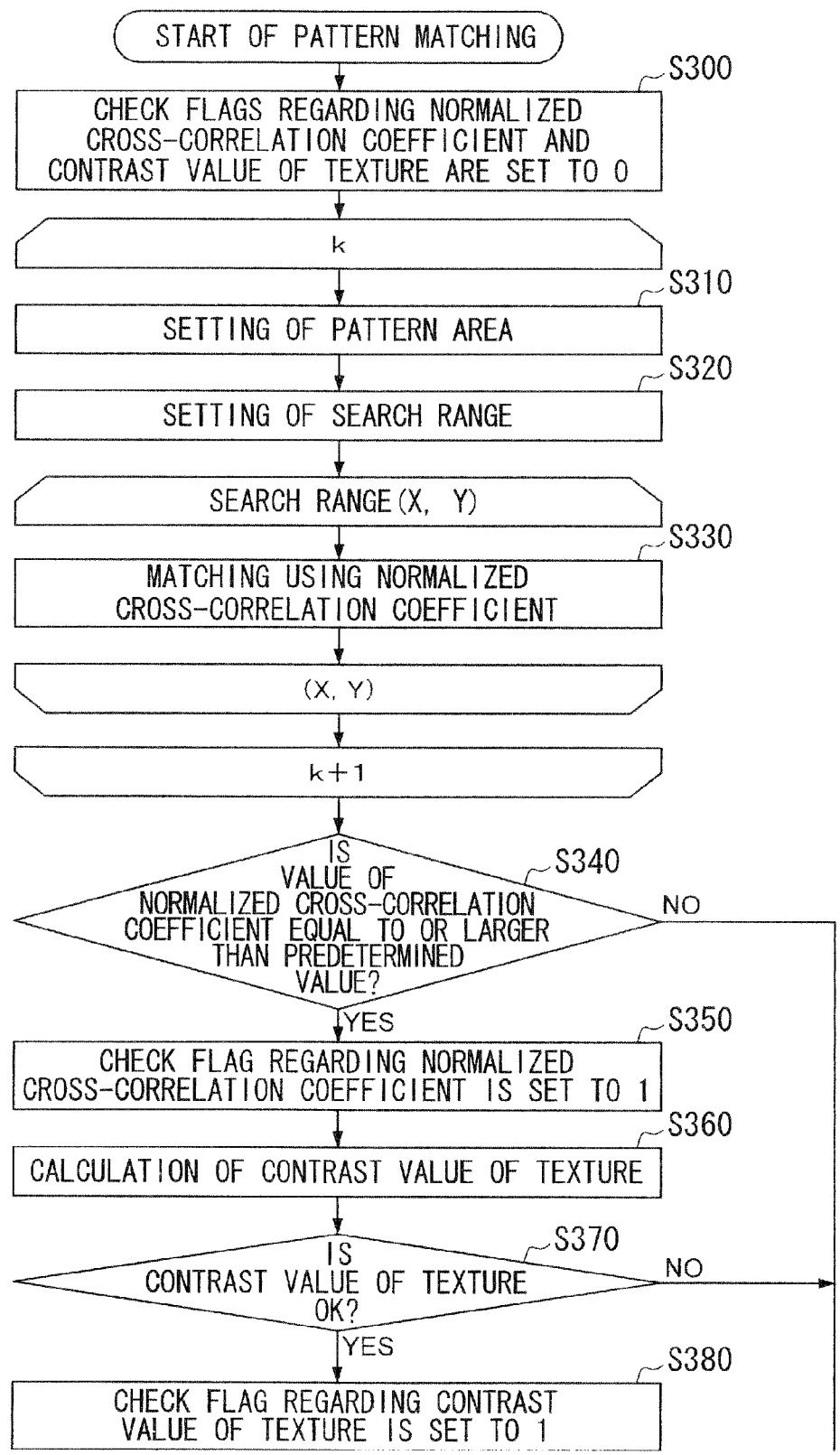
FIG. 10 is a flow chart illustrating the procedure of pattern matching processing (first operation example) executed by a measuring endoscope apparatus according to an embodiment of the invention.

Next, details of the pattern matching processing in step S200 will be described. As shown in FIG. 10, as initialization processing, the CPU 18 first sets a value of a check flag regarding a normalized cross-correlation coefficient and a value of a matching check flag regarding a contrast value of a texture to 0 (step S300).

Then, the CPU 18 narrows a pattern area indicating the size of a pattern on which the pattern matching is performed (step S310). In an example of the present embodiment, a pattern area corresponding to a value k is set. That is, assuming that the pattern area is set to have 35×35 (pixels) in the case of k=1, the pattern area is set to have 23×23 (pixels) in the case of k=2, and the pattern area is set to have 11×11 (pixels) in the case of k=3, the area is decreased by increasing the value k so that the accuracy of corresponding point detection can be raised.

Then, the CPU 18 sets a search range. That is, a region of the right image where a pattern is searched is determined (step S320). Examples of setting the search range include, in consideration of an error in the epipolar line, a case where the search range is set within epipolar line±5 pixels, a case where the search range is set within ±7 pixels horizontally on a monitor screen, and a case where the search range is set within ±10 pixels with respect to an approximate matching point instructed manually on the screen. In addition, the ±10 pixels are the optimal value in consideration of an error caused by the manual operation.

Then, the CPU 18 performs pattern matching in the set search range (step S330). In this pattern matching, detection of a corresponding point using normalized cross correlation is performed to set coordinates (X, Y) with the largest normalized cross-correlation coefficient (−1~+1) as the corresponding point. The pattern matching is repeatedly performed while incrementing the value k to narrow a pattern corresponding to the value k and moving the pattern area within the search range.

For a normalized cross-correlation function M(u, v) used in pattern matching, the following expression is generally used. That is, assuming that t(x, y) is a template, g(x, y) is image data, t' is the average brightness of the template, and g' is the average brightness of the image, the following expression (3) is applied. Here, $\Sigma\Sigma_s$ means the sum of pixels.

$$M(u,v) = \{\Sigma\Sigma_s(g(x+u,y+v)-g')(t(x,y)-t')\}/\{\Sigma\Sigma_s(g(x+u,y+v)-g')^2 \times \Sigma\Sigma_s(t(x,y)-t')^2\}^{1/2} \quad (3)$$

After the pattern matching is completed, the CPU 18 determines a value of the normalized cross-correlation coefficient (step S340). The value of the normalized cross-correlation coefficient used in the determination is a value considered to be largest in the pattern matching.

When the value of the normalized cross-correlation coefficient is a predetermined value or more, the process proceeds to step S350. When the value of the normalized cross-correlation coefficient is less than the predetermined value, the pattern matching processing is ended. When the value of the normalized cross-correlation coefficient is the predetermined value or more, the CPU 18 sets a value of a check flag regarding the normalized cross-correlation coefficient to 1 (step S350). Then, the CPU 18 calculates a contrast value of a texture (step S360).

An image region for calculating the contrast value of the texture is assumed to be 11×11 pixels which is the size of the pattern area where the pattern matching has been performed. A contrast value C(d, θ) of the texture is generally calculated as follows. A co-occurrence matrix D(a, b;d, θ) is expressed as an intensity pair (a, b) of a pixel pair [(x, y), (u, v)] which is in the specific relative positional relationship (d, θ) (d is a distance and θ is an angle). In this case, f(x, y)=a and f(u, v)=b are assumed. When 'L' kinds of pixels of 0 to L−1 exist, D(a, b;d, θ) becomes a matrix of L×L. That obtained by normalizing D such that the sum of all elements becomes 1 is expressed as the following expression (4). In this case, $N_L = \{0, 1, 2, \ldots, L-1\}$.

$$k(a, b; d, \theta) = \frac{D(a, b; d, \theta)}{\sum_{a \in N_L} \sum_{b \in N_L} D(a, b; d, \theta)} \quad (4)$$

The contrast value of the texture is expressed as the following expression (5).

$$C(d, \theta) = \sum_{a \in N_L} \sum_{b \in N_L} \{(a-b)^2 \times k(a, b; d, \theta)\} \quad (5)$$

Then, the CPU 18 determines the contrast value of the texture (step S370). When a difference between the contrast values of the texture in the left and right images is less than a predetermined value, the process proceeds to step S380. In other case, the pattern matching processing is ended. When the difference between the contrast values of the texture in the left and right images is less than the predetermined value, the CPU 18 sets a value of a check flag regarding the contrast value of the texture to 1 (step S380).

In the first operation example described above, three kinds of determinations (determination on a value of a normalized cross-correlation coefficient, determination on a contrast value of a texture, and determination on the object distance) on the reliability of matching processing are performed, and the distance between two points is calculated and the measurement result is displayed when it is determined that the result of the matching processing is reliable in all of the determinations. In addition, when it is determined that the result of the matching processing is not reliable in at least one of the determinations, a measurement result showing that the matching processing has failed is displayed.

In addition, the processing shown in FIG. 6 may be performed as follows. After performing the three-dimensional coordinate analysis processing regarding the first measurement point (step S110), the CPU 18 determines whether or not the matching processing has been successful on the basis of a value of the matching check flag (the same processing as step S140). When the value of the matching check flag is 1, the process proceeds to step S120. When the value of the matching check flag is 0, the process proceeds to step S100. That is, setting of the first measurement point and three-dimensional coordinate analysis processing are repeated until the matching processing performed in the three-dimensional analysis processing regarding the first measurement point is successful.

Moreover, in the determination on the reliability of the matching processing, the parallax of a corresponding point on the right image corresponding to a measurement point on the left image from the epipolar line may also be used. For example, it is determined that the matching processing has failed when the coordinates of the corresponding point on the right image calculated by the matching processing deviate from the epipolar line by a predetermined value or more.

Figure 11:
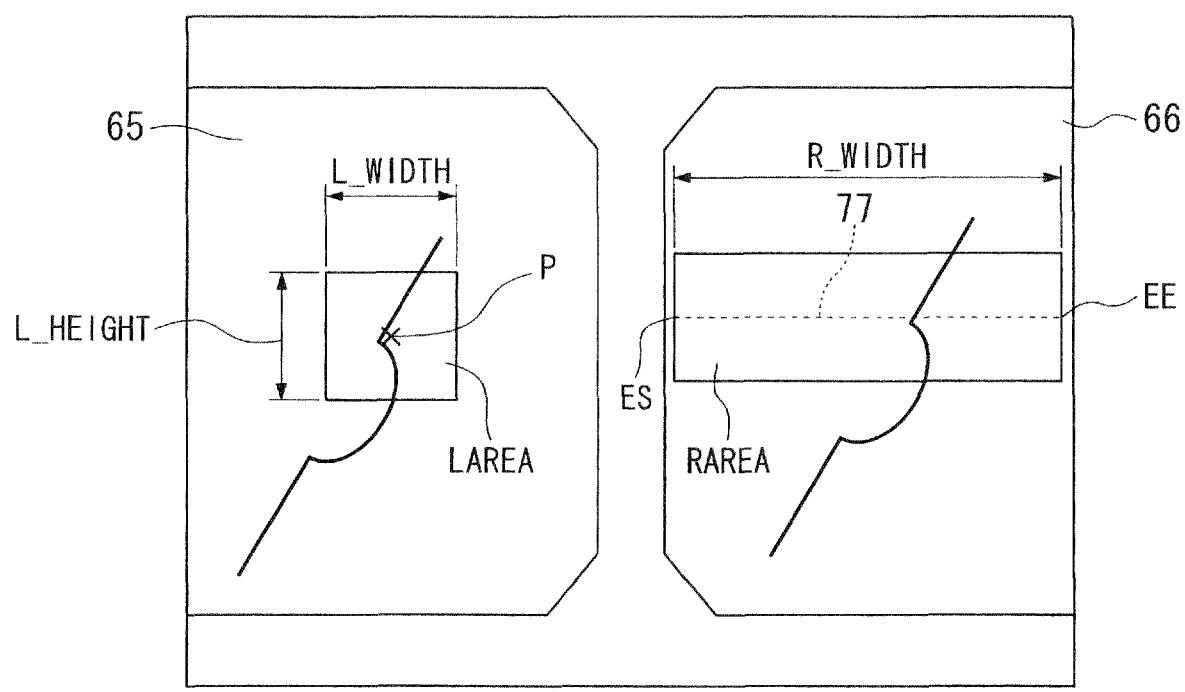
FIG. 11 is a reference drawing illustrating how to calculate the epipolar line in an embodiment of the invention.

A specific method of calculating the epipolar line is as follows. As shown in FIG. 11, a capture range of a left image 65 in the present embodiment is an image near a distance measurement point P. In FIG. 11, assuming that the coordinates of the distance measurement point P is (lx, ly), a left acquisition width is L_WIDTH, and a left acquisition height is L_HEIGHT, the coordinates of a base point SPL of an acquisition range LAREA of the left image is set to (lx−L_WIDTH/2, ly−L_HEIGHT/2). In addition an acquisition range RAREA of a right image 66 is an image near an epipolar line 77, as shown in FIG. 11.

The epipolar line 77 is calculated as follows. Coordinates of a left reference point OL and coordinates of a right reference point OR are read from optical data. The left reference point OL and the right reference point OR are coordinates of the same object to be observed near the optical center and are set when optical data is created. Assuming that the coordinates of the left reference point OL is (olx, oly), and the coordinates of the right reference point OR is (orx, ory).

Assuming that the X coordinate at the left end of the right image 66 is rsx, the coordinates (esx, esy) of a starting point ES of the epipolar line becomes (esx, esy)=(rsx, ly−oly+ory). In addition, the coordinates (eex, cey) of an end point EE of the epipolar line becomes (eex, eey)=(rsx+R_WIDTH, ly−oly+ory), assuming that the acquisition width is R_WIDTH.

Accordingly, assuming that the acquisition height is R_HEIGHT, the coordinates of a base point SPR of the acquisition range RAREA of the right image 66 becomes (esx, esy−R_HEIGHT/2) In addition, the method of calculating the epipolar line is not limited to that described above, and other calculating methods which are known in a general stereo vision field may also be adopted.

SECOND OPERATION EXAMPLE

Figure 12:
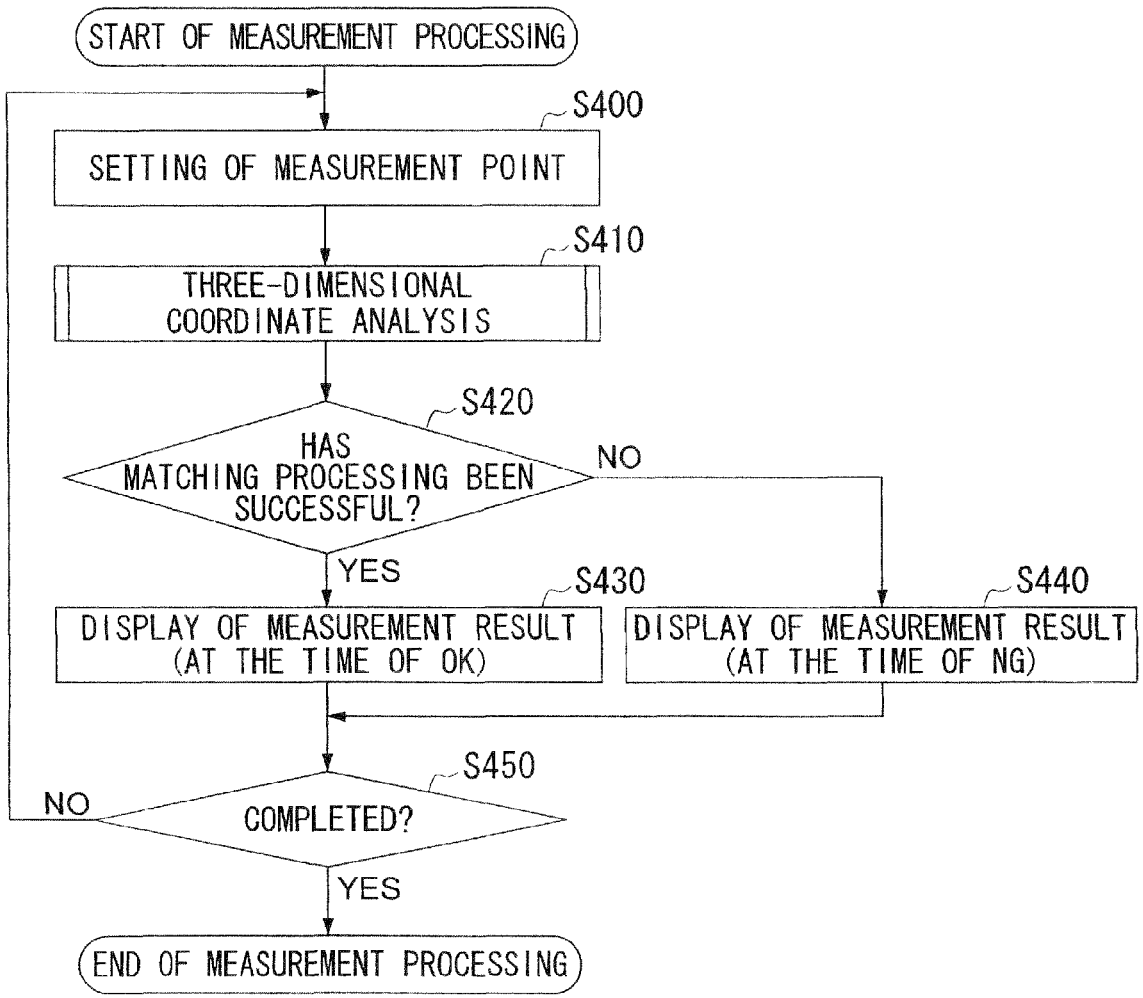
FIG. 12 is a flow chart illustrating the procedure of measurement processing (second operation example) executed by a measuring endoscope apparatus according to an embodiment of the invention.

Next, as a second operation example of measurement processing, an operation in measuring the object distance will be described. As shown in FIG. 12, first, a measurement point is set (step S400), and the three-dimensional coordinate analysis processing is executed to calculate the three-dimensional coordinates of the measurement point (step S410). The three-dimensional coordinate analysis processing is the same as that in the first operation example. Then, the CPU 18 determines whether or not matching processing has been successful on the basis of a value of a matching check flag (step S420). When the value of the matching check flag is 1, it is determined that the matching processing executed as a part of step S410 is successful, proceeding to step S430. In addition, when the value of the matching check flag is 0, it is determined that the matching processing executed as a part of step S410 has failed, proceeding to step S440.

When the matching processing executed as a part of step S410 is successful, the value of the matching check flag becomes 1. In this case, the CPU 18 makes a control of displaying, as a measurement result, the object distance calculated in the three-dimensional coordinate analysis processing of step S410 (step S430). In addition, when the matching processing executed as a part of step S410 has failed, the CPU 18 makes a control of displaying a failure of the matching processing as a measurement result (step S440). A method of displaying the measurement result is the same as that in the first operation example.

Figure 13A:
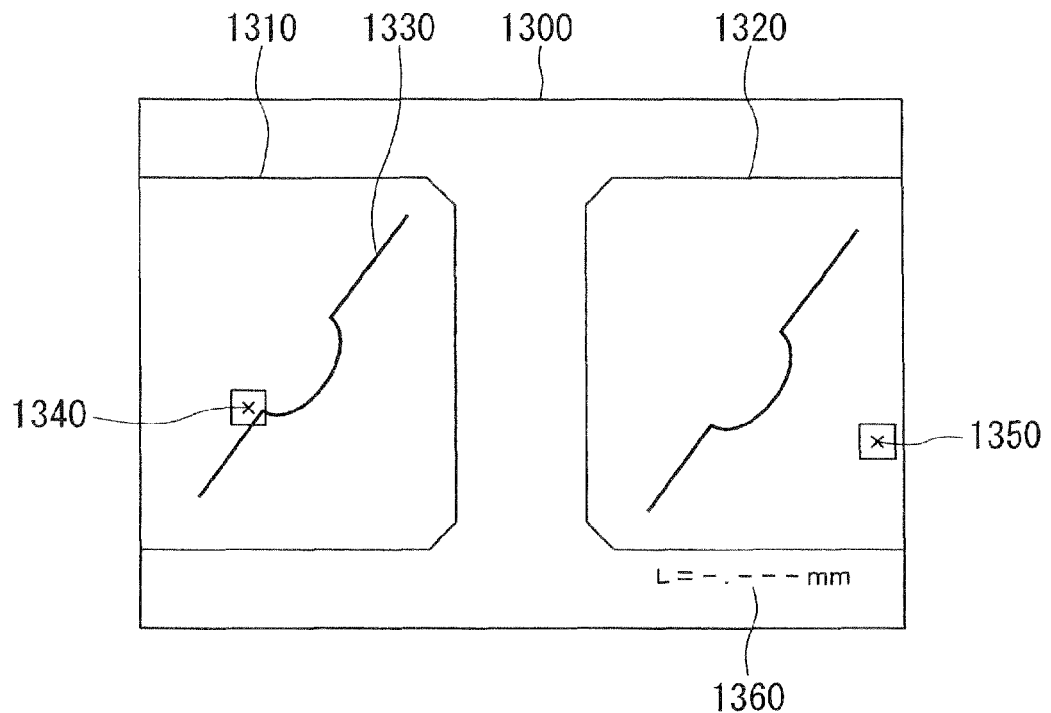
FIGS. 13A and 13B are reference views illustrating a display screen (second operation example) of a measuring endoscope apparatus according to an embodiment of the invention.
Figure 13B:
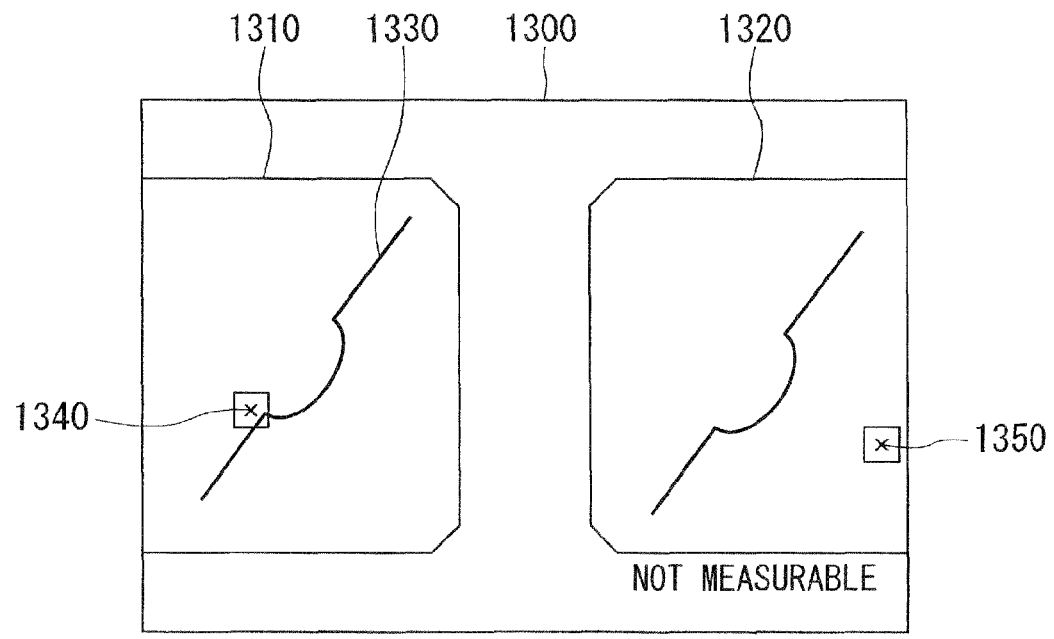

FIGS. 13A and 13B show display screens of the monitor 4. A left image 1310 and a right image 1320 corresponding to left and right subject images captured by the optical adapter 46 are displayed on a display screen 1300 shown in FIGS. 13A and 13B. When a user designates a measurement point 1340 on a subject 1330 of the left image 1310, the position of a corresponding point 1350 on the right image 1320, which corresponds to the measurement point 1340, is calculated by matching processing. As shown in FIGS. 13A and 13B, when the calculation accuracy of the measurement point 1350 is low, a measurement result 1360 is displayed like "-.---" (FIG. 13A) or "not measurable" (FIG. 13B) indicating a failure of the matching processing.

Subsequent to steps S430 and S440, the CPU 18 determines whether or not the measurement processing has been completed (step S450). When the user has input an instruction to end the measurement processing by operating the operating portion 6, the measurement processing is ended. In other cases, the processing returns to step S400, and various processing is executed on the basis of endoscope image data newly acquired from the video signal processing circuit 12.

THIRD OPERATION EXAMPLE

Figure 14:
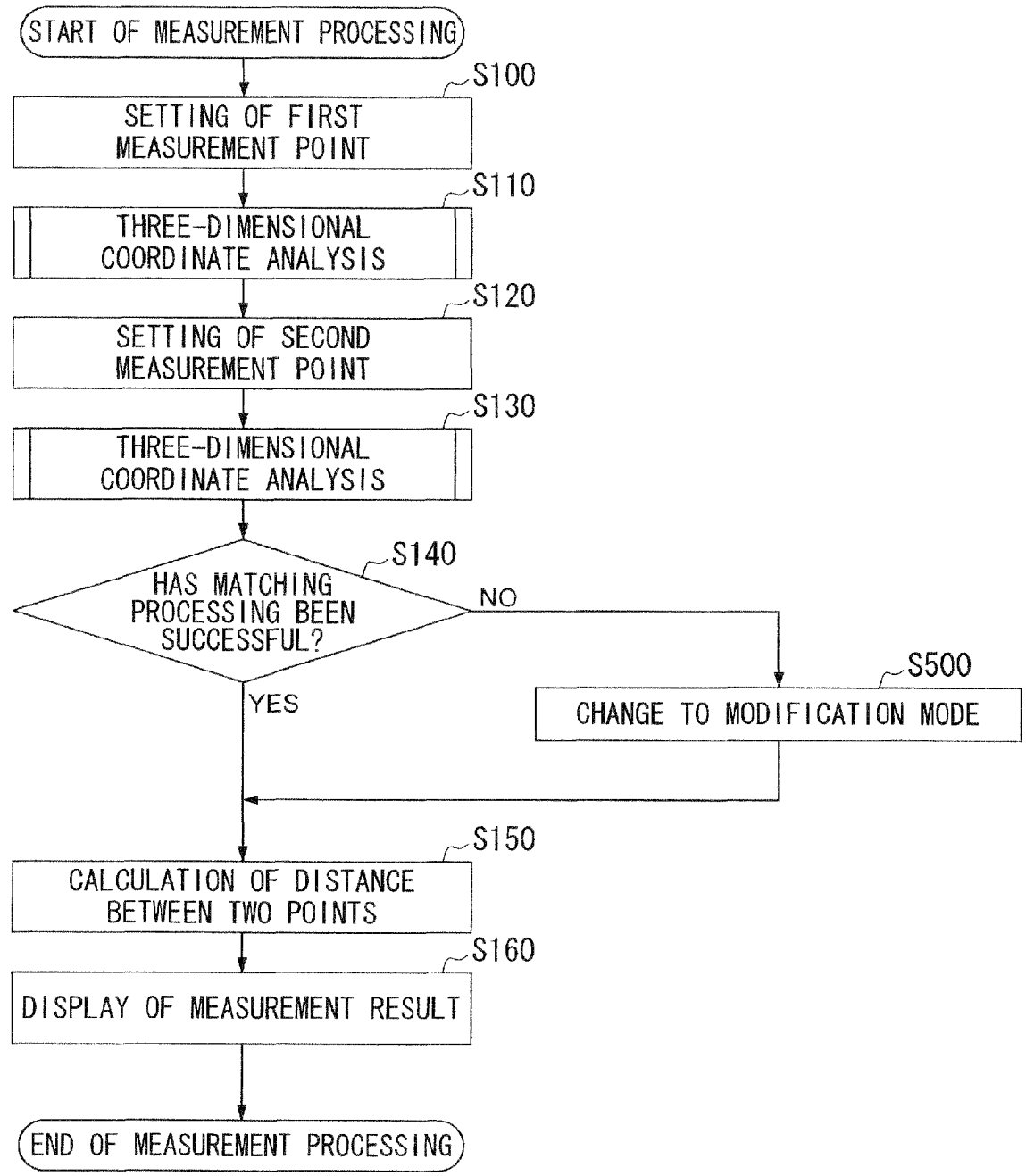
FIG. 14 is a flow chart illustrating the procedure of measurement processing (third operation example) executed by a measuring endoscope apparatus according to an embodiment of the invention.

Next, a third operation example regarding the measurement processing will be described. The operation in measuring the distance between two points, which was explained in the first operation example, will now be described. However, the operation in measuring the object distance explained in the second operation example is also the same. FIG. 14 shows processing in the third operation example. The same processing as the processing shown in FIG. 6 is denoted by the same reference numeral. In processing shown in FIG. 14, when a value of at least one of the two kinds of matching check flags is 0 as a result of checking the values of the matching check flags in step S140, the CPU 18 executes a control of changing to a modification mode in which a measurement point is modified (step S500).

When the operation mode of the measuring endoscope apparatus 1 changes to the modification mode, the user can modify the position of the corresponding point on the right image manually by operating the operating portion 6. The modification mode itself is also prepared in a known measuring endoscope apparatus. After modification of the corresponding point is completed, the three-dimensional coordinates are calculated on the basis of the position of the corresponding point after modification. Then, calculation of the distance between two points and display of the measurement result are performed (steps S150 and S160). As a result, an improvement in the reliability of the measurement result can be expected. Moreover, in the processing shown in FIG. 14, a change to the modification mode may also be made while displaying the measurement result showing that the matching processing has failed by performing the processing of step S170 shown in FIG. 6.

FOURTH OPERATION EXAMPLE

Next, a fourth operation example regarding the measurement processing will be described. The operation in measuring the distance between two points, which was explained in the first operation example, will now be described. However, the operation in measuring the object distance explained in the second operation example is also the same. In the fourth operation example, it is possible to select a mode in which a determination on the reliability of the matching processing (hereinafter, referred to as a matching reliability determination) is performed and a mode in which a determination is not performed. One of the two modes is set in advance before the measurement processing starts. Alternatively, the mode may be set immediately after the start of the measurement processing.

Figure 15:
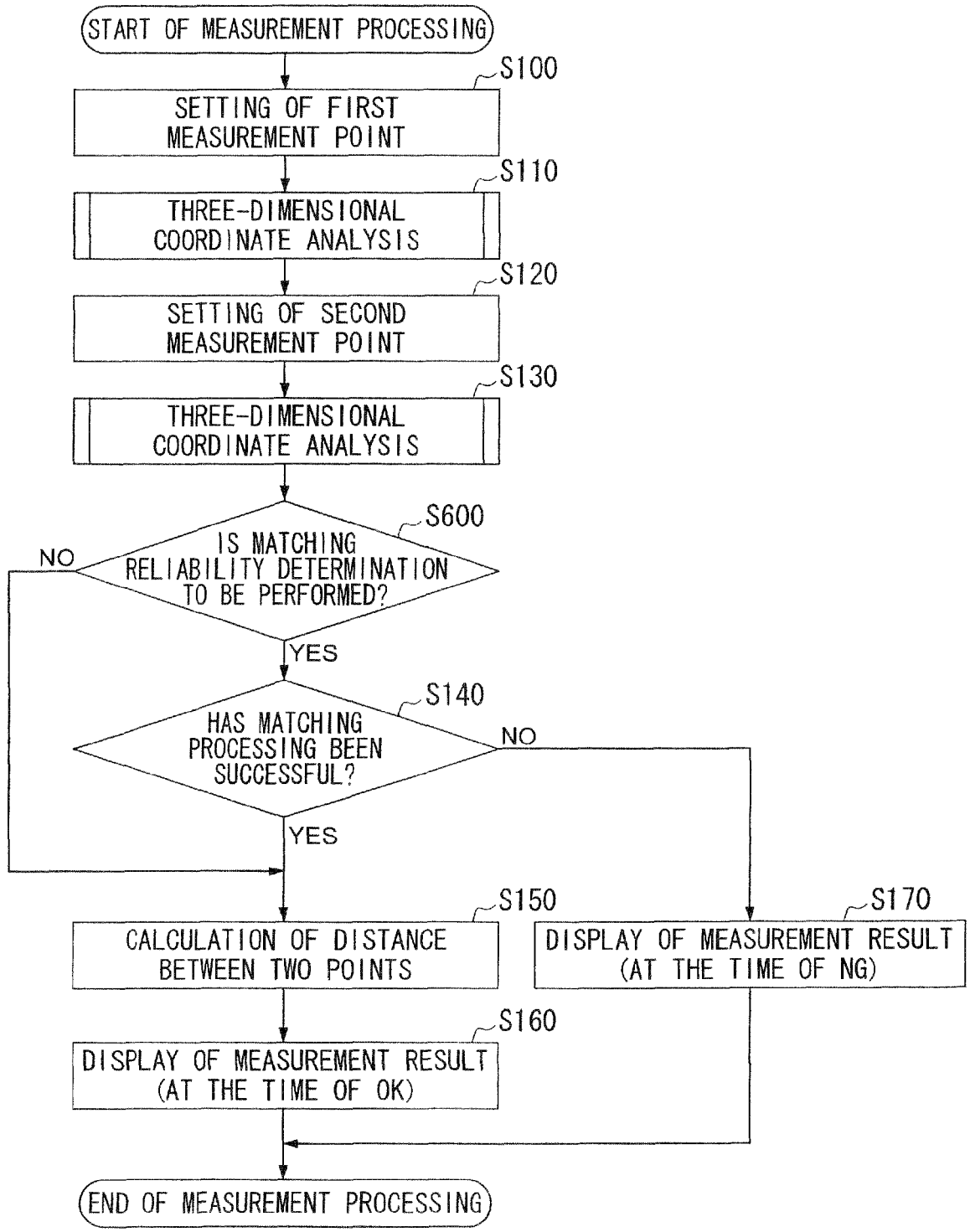
FIG. 15 is a flow chart illustrating the procedure of measurement processing (fourth operation example) executed by a measuring endoscope apparatus according to an embodiment of the invention.

FIG. 15 shows processing in the fourth operation example. The same processing as the processing shown in FIG. 6 is denoted by the same reference numeral. In the processing shown in FIG. 15, after performing the three-dimensional coordinate analysis processing in step S130, the CPU 18 determines whether or not to perform the matching reliability determination (step S600). When it is set to perform the matching reliability determination, the process proceeds to step S140. When it is set not to perform the matching reliability determination, the process proceeds to step S150.

Figure 16:
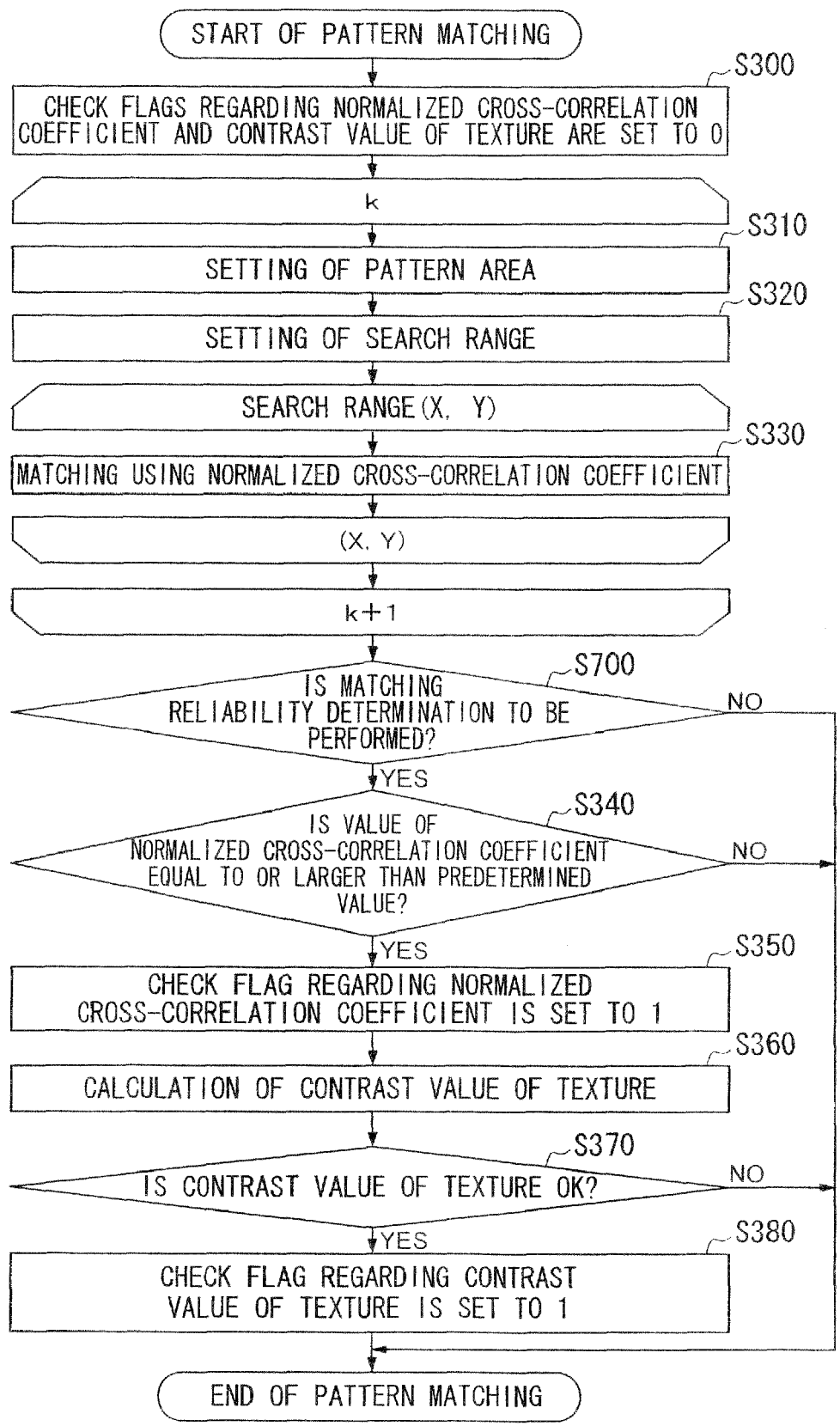
FIG. 16 is a flow chart illustrating the procedure of pattern matching processing (fourth operation example) executed by a measuring endoscope apparatus according to an embodiment of the invention.

FIG. 16 shows pattern matching processing in the fourth operation example. The same processing as the processing shown in FIG. 10 is denoted by the same reference numeral. In the processing shown in FIG. 16, after performing the pattern matching in steps S3110 to S330, the CPU 18 determines whether or not to perform the matching reliability determination (step S700). When it is set to perform the matching reliability determination, the process proceeds to step S340. When it is set not to perform the matching reliability determination, the pattern matching processing is ended. Since processing on the matching reliability determination is excluded in the case where it is set not to perform the matching reliability determination, the processing can be performed quickly.

FIFTH OPERATION EXAMPLE

Next, a fifth operation example regarding the measurement processing will be described. In the above operation examples, the display order of a measurement result and the like when it is determined that the result of the matching processing is not reliable is not specified. However, in order to improve working efficiency, it is preferable to display the measurement result indicating that the matching processing has failed earlier. For this reason, in the fifth operation example, the measurement result is displayed earlier than other things when it is determined that the result of the matching processing is not reliable. The operation in measuring the distance between two points, which was explained in the first operation example, will now be described. However, the operation in measuring the object distance explained in the second operation example is also the same.

Figure 17A:
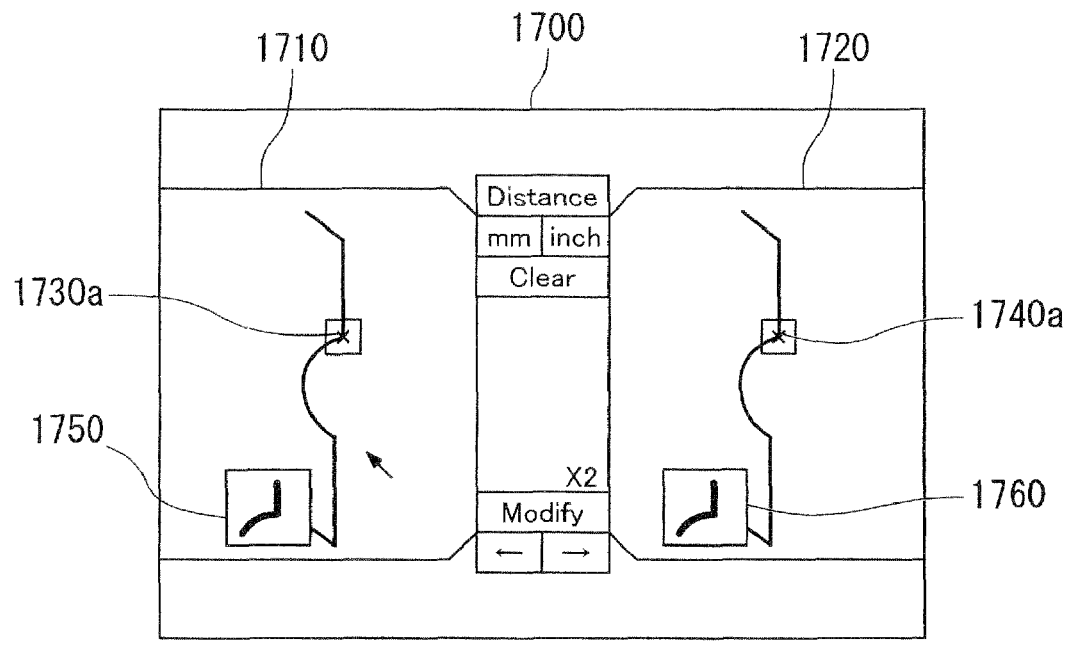
FIGS. 17A and 17B are reference views illustrating a display screen (fifth operation example) of a measuring endoscope apparatus according to an embodiment of the invention.
Figure 17B:
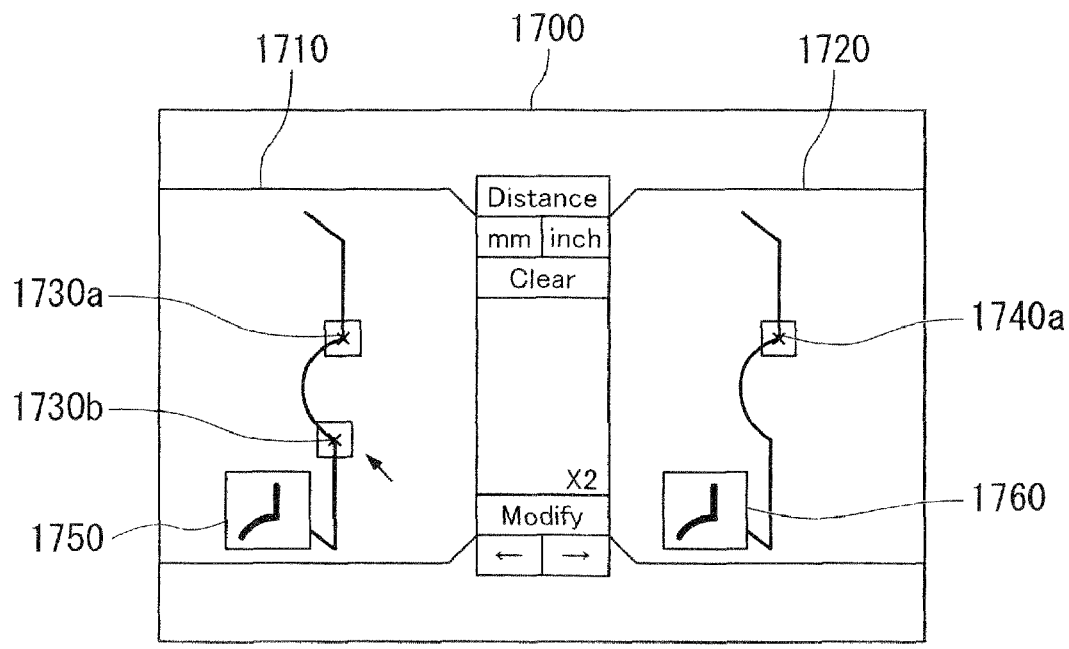

As shown in FIG. 17A, first, when a first measurement point 1730*a* is set on a left image 1710 of a display screen 1700, a first corresponding point 1740*a* on a right image 1720 corresponding to the first measurement point 1730*a* is set. At this time, an enlarged image at the first measurement point 1730*a* is displayed on a zoom window 1750, and an enlarged image at the first corresponding point 1740*a* is displayed on a zoom window 1760. Then, as shown in FIG. 17B, a second measurement point 1730*b* is set on the left image 1710. At this time, the CPU 18 executes a control of additionally displaying the second measurement point 1730*b* on the display screen 1700. In addition, the CPU 18 executes processing of step S130 and the subsequent steps shown in FIG. 6 in addition to the control of displaying the second measurement point 1730*b*.

Figure 18A:
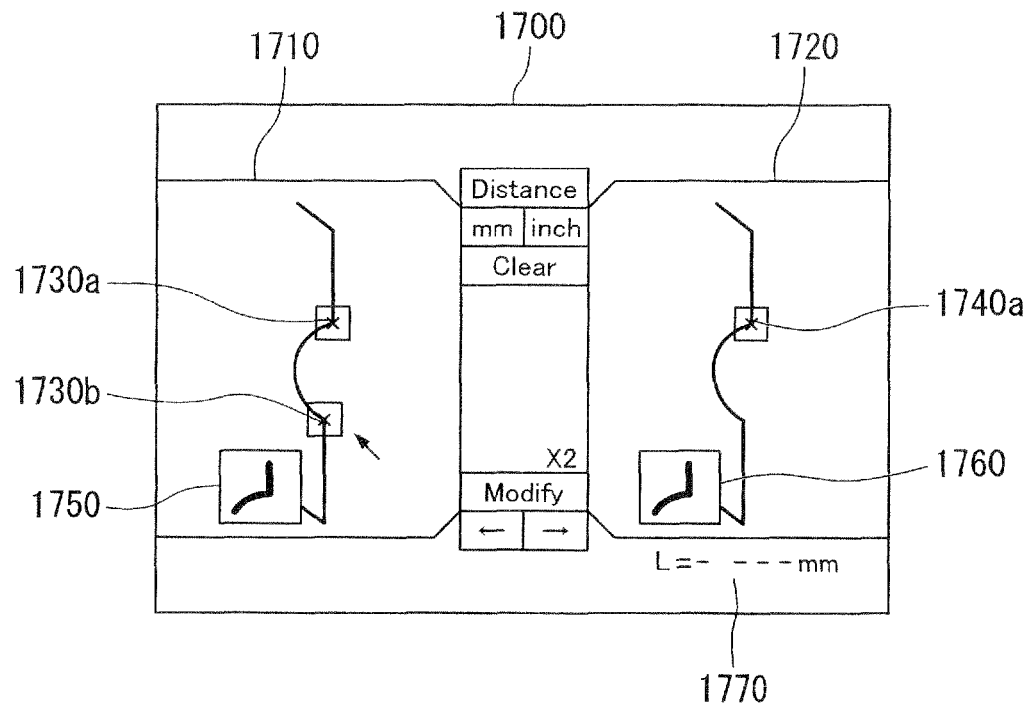
FIGS. 18A and 18B are reference views illustrating a display screen (fifth operation example) of a measuring endoscope apparatus according to an embodiment of the invention.
Figure 18B:
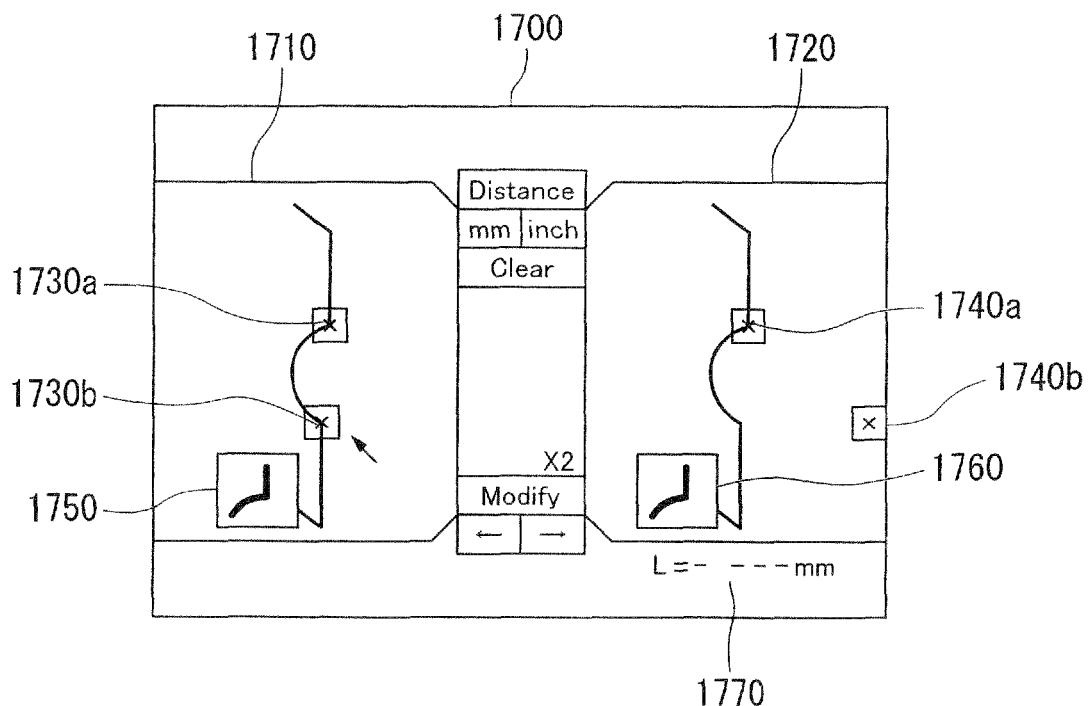
Figure 19A:
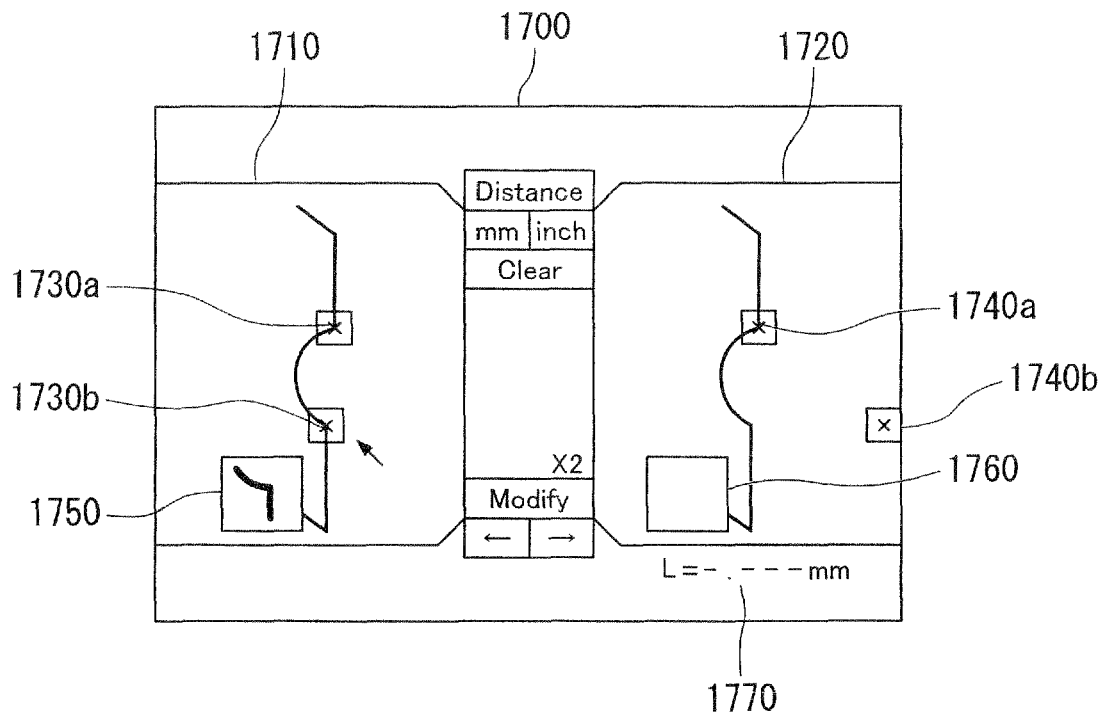
FIGS. 19A and 19B are reference views illustrating a display screen (fifth operation example) of a measuring endoscope apparatus according to an embodiment of the invention.
Figure 19B:
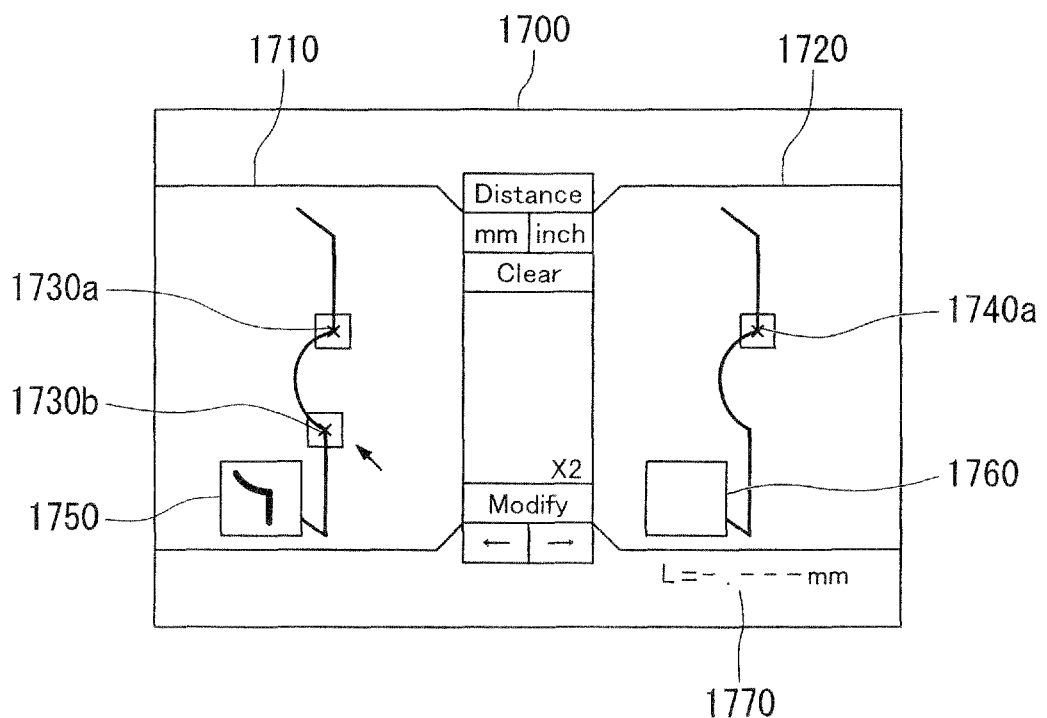

When it is determined that the matching processing has failed as a result of the processing in step S140 shown in FIG. 6, the CPU 18 executes a control of additionally displaying a measurement result indicating a failure of the matching processing on the display screen 1700. As a result, a measurement result 1770 is displayed as shown in FIG. 18A. Then, the CPU 18 executes a control of additionally displaying, on the display screen 1700, a second corresponding point on the right image 1720 corresponding to the second measurement point 1730*b*. As a result, a second corresponding point 1740*b* is displayed on the right image 1720 as shown in FIG. 18B. When the matching reliability determination is performed earlier than the three-dimensional coordinate analysis processing like a sixth operation example to be described later, the second corresponding point 1740*b* may be displayed at a predetermined position without calculating the actual position of the second corresponding point 1740*b*, or a control may be made such that the second corresponding points 1740*b* is not displayed on the right image 1720 (FIG. 19B).

Then, CPU 18 executes a control of displaying an enlarged image at the second measurement point 1730*b* on the left image 1710 in the zoom window 1750 and displaying an enlarged image at the second corresponding point 1740*b* on the right image 1720 in the zoom window 1760. As a result, display of the zoom windows 1750 and 1760 is updated as shown in FIG. 19A. When a control is made such that the second corresponding point 1740*b* is not displayed, the enlargement image is not displayed in the zoom window 1760. As described above, by performing processing for displaying a measurement result earlier than processing for displaying the corresponding point on the right image corresponding to the measurement point on the left image or processing for displaying the enlarged image at the measurement point in the zoom window when it is determined that the result of matching processing is not reliable, it is possible to inform the user earlier that the matching processing has failed. As a result, working efficiency can be improved.

To sum up, it is preferable that the processing for displaying the measurement result indicating that the matching processing has failed be performed earlier than the processing for displaying a region including the corresponding point on the right image corresponding to the measurement point on the left image. The region including the corresponding point on the right is at least one of a region at the second corresponding point 1740*b* on the right image 1720 shown in FIGS. 19A and 19B and its peripheral region (region where a graphic including the second corresponding point 1740*b* is displayed), a region including the zoom window 1760, and the entire right image 1720.

SIXTH OPERATION EXAMPLE

Next, a sixth operation example regarding the measurement processing will be described. The operation in measuring the object distance explained in the second operation example will now be described. However, the operation in measuring the distance between two points, which was explained in the first operation example, is also the same. In the sixth operation example, the matching reliability determination is performed before the three-dimensional coordinate analysis processing.

Figure 20:
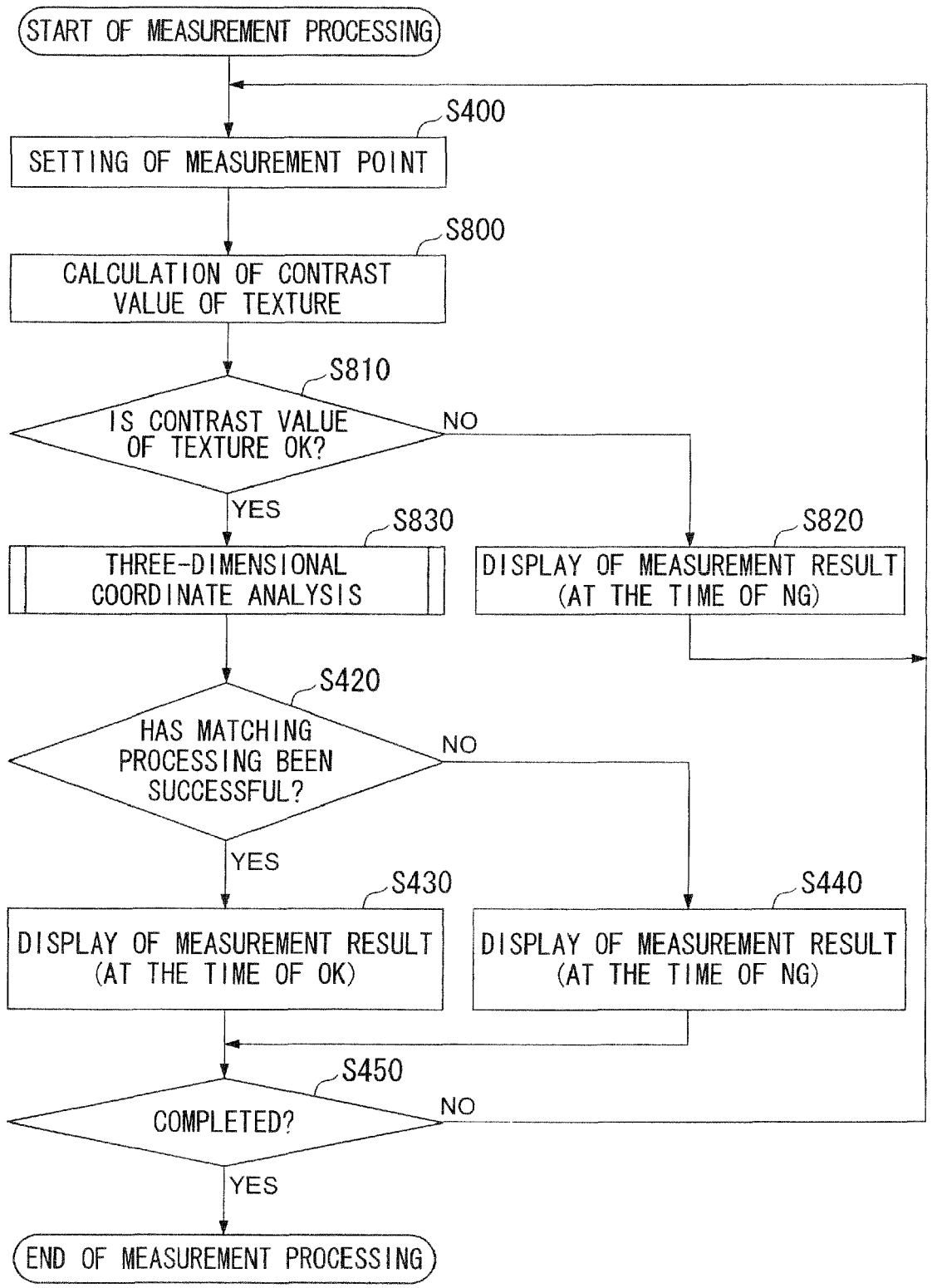
FIG. 20 is a flow chart illustrating the procedure of measurement processing (sixth operation example) executed by a measuring endoscope apparatus according to an embodiment of the invention.

FIG. 20 shows measurement processing corresponding to FIG. 12. The same processing as the processing shown in FIG. 12 is denoted by the same reference numeral. FIG. 20 is different from FIG. 12 in that processing of steps S800 to S820 is added and the processing of step S410 is replaced with processing of step S830. After a measurement point is set in step S400, the CPU 18 calculates a contrast value of a texture (step S800). At this time, the CPU 18 calculates a contrast value of a texture from an image of the pattern area of 11×11 pixels around the measurement point set on the left image.

Then, the CPU 18 determines the contrast value of the texture (step S810). In this determination, it is determined whether or not the image is suitable for the measurement (particularly the matching processing) by comparing the contrast value of the texture calculated in step S800 with a predetermined value. When the contrast value of the texture is the predetermined value or more, the process proceeds to step S830. In addition, when the contrast value of the texture is less than the predetermined value, the image is not suitable for the measurement. Accordingly, in this case, the CPU 18 executes a control of displaying as a measurement result that the image is not suitable for the measurement (step S820).

Figure 21:
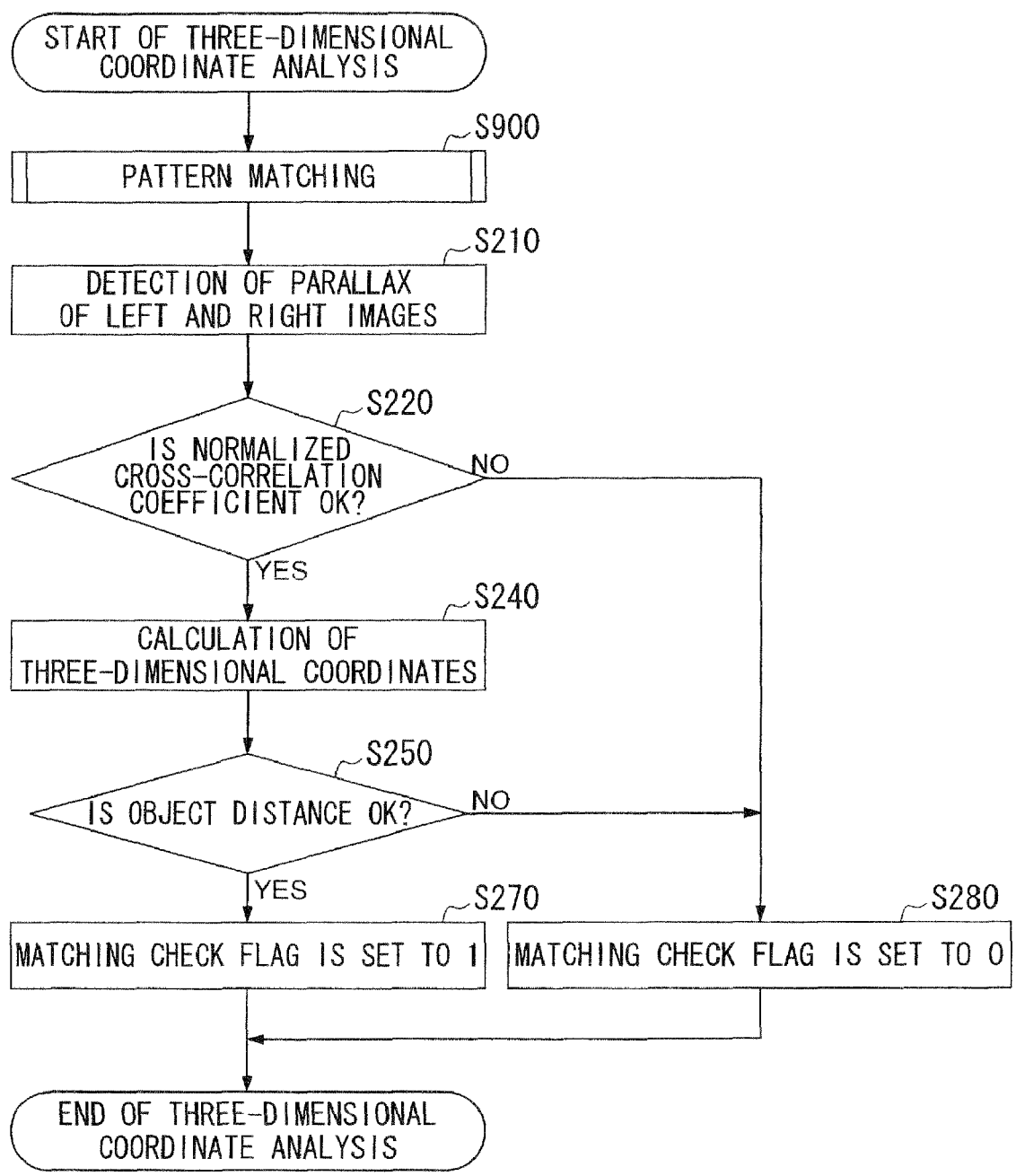
FIG. 21 is a flow chart illustrating the procedure of three-dimensional coordinate analysis processing (sixth operation example) executed by a measuring endoscope apparatus according to an embodiment of the invention.
Figure 22:
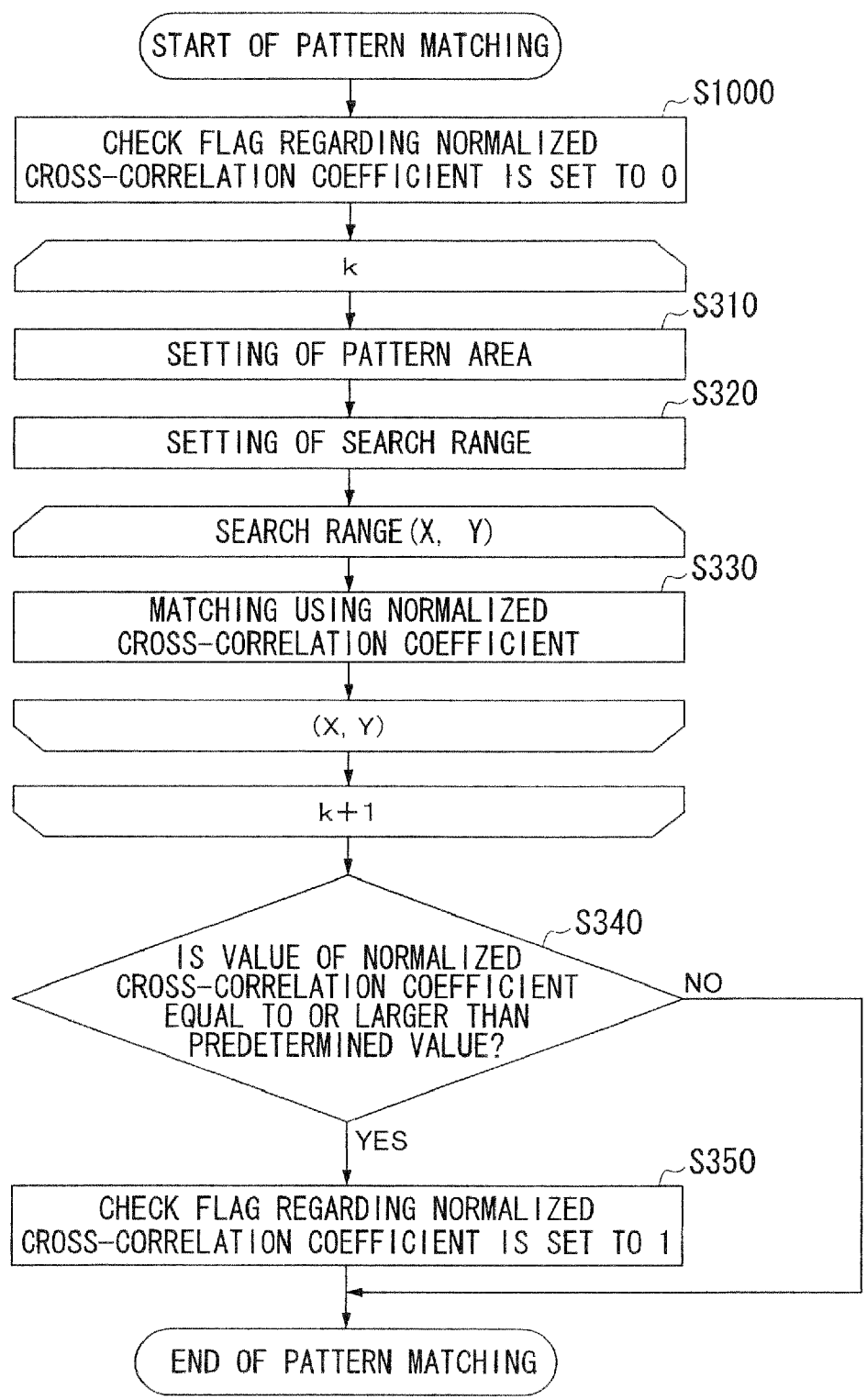
FIG. 22 is a flow chart illustrating the procedure of pattern matching processing (sixth operation example) executed by a measuring endoscope apparatus according to an embodiment of the invention.

FIG. 21 shows three-dimensional coordinate analysis processing in step S830. The same processing as the processing shown in FIG. 8 is denoted by the same reference numeral. FIG. 21 is different from FIG. 8 in that the processing of step S230 regarding the contrast value of the texture is excluded and the processing of step S200 shown in FIG. 8 is replaced with processing of step S900. FIG. 22 shows pattern matching processing in step S900. The same processing as the processing shown in FIG. 10 is denoted by the same reference numeral. FIG. 22 is different from FIG. 10 in that the processing of steps S360 to S380 regarding the contrast value of the texture is excluded and the processing of step S300 shown in FIG. 10 is replaced with processing of step S1000. In step S1000, the CPU 18 sets a value of a check flag regarding a normalized cross-correlation coefficient to 0 as initialization processing.

As described above, by performing the matching reliability determination before the three-dimensional coordinate analysis processing using the contrast value of the texture which can be calculated even if the pattern matching processing is not performed, it is possible to inform the user earlier that the reliability of the matching processing is low. As a result, working efficiency can be improved. In addition, since the matching reliability determination on the object distance and the matching reliability determination on the normalized cross-correlation coefficient are performed after the matching processing for calculating the position of the corresponding point on the right image corresponding to the measurement point on the left image, the accuracy of matching reliability determination can be maintained.

SEVENTH OPERATION EXAMPLE

Next, a seventh operation example regarding the measurement processing will be described. The operation in measuring the object distance explained in the second operation example will now be described. However, the operation in measuring the distance between two points, which was explained in the first operation example, is also the same. In the seventh operation example, matching reliability determination is performed while a user is moving a pointer to designate the position of a measurement point.

Figure 23:
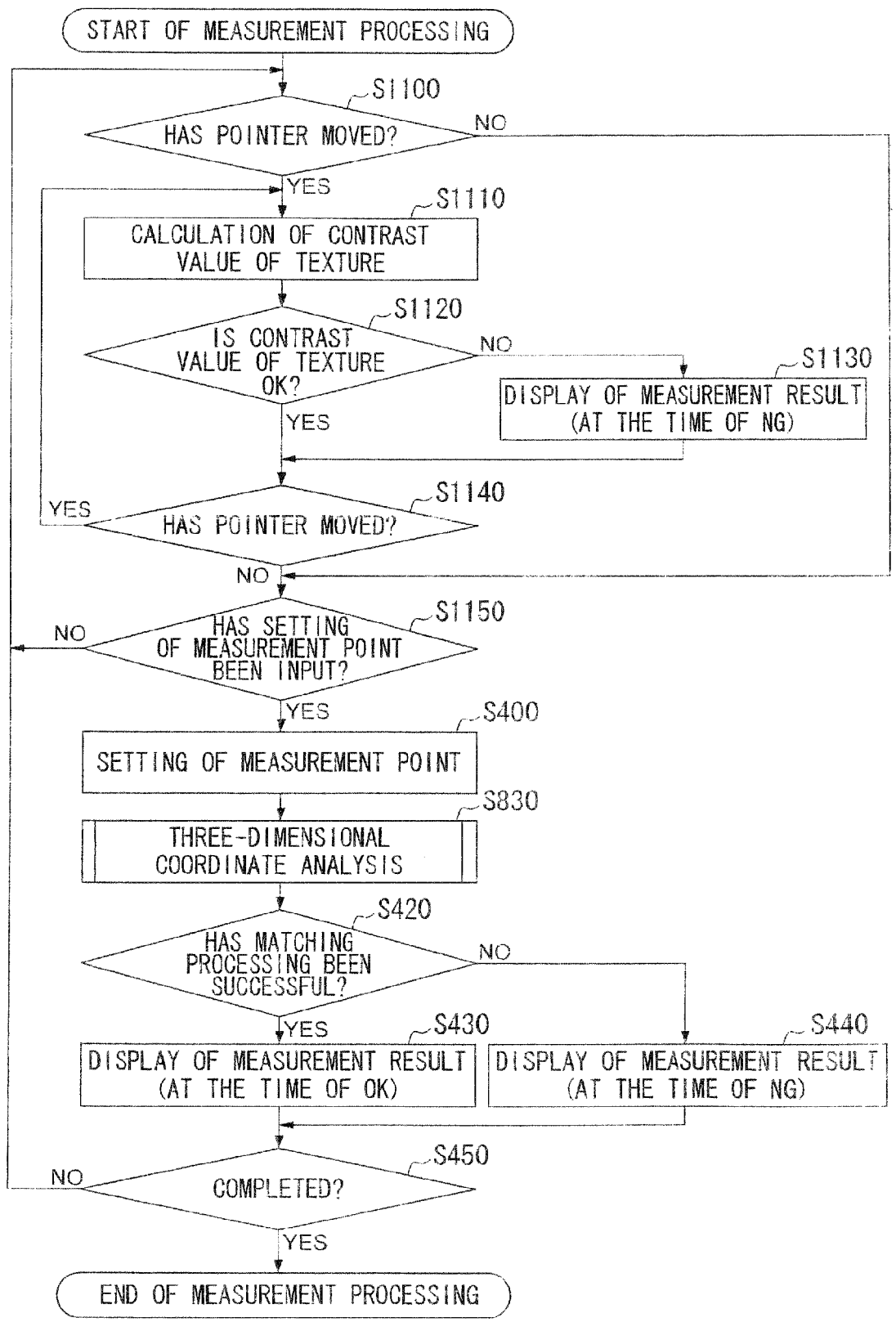
FIG. 23 is a flow chart illustrating the procedure of measurement processing (seventh operation example) executed by a measuring endoscope apparatus according to an embodiment of the invention.
Figure 24:
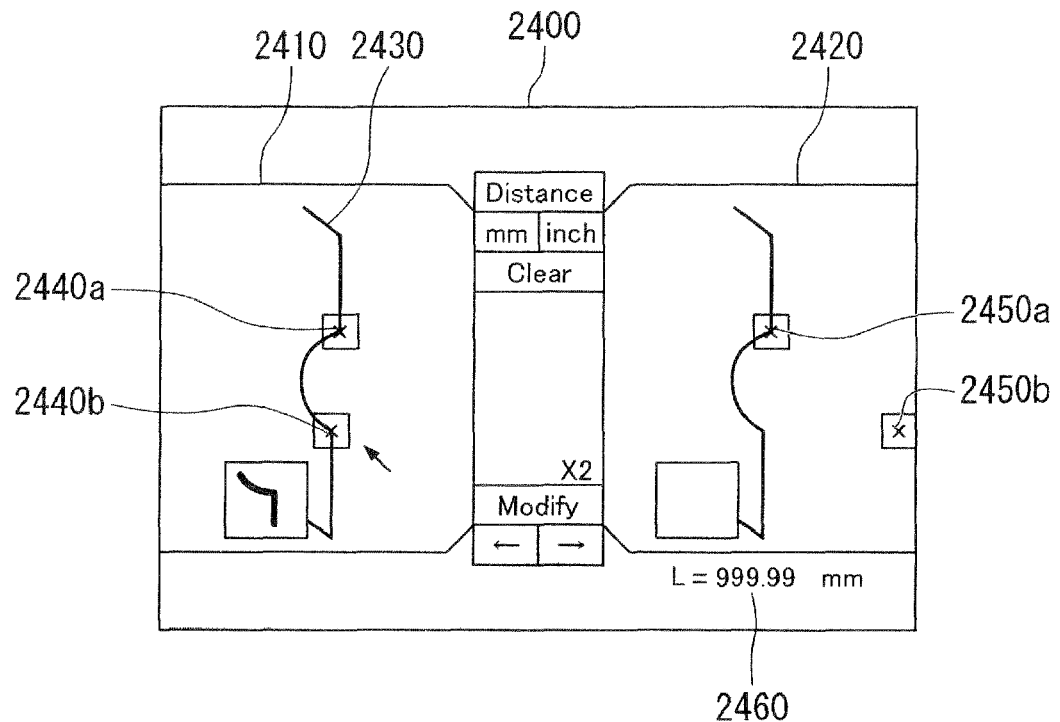
FIG. 24 is a reference view illustrating a display screen of a known measuring endoscope apparatus.
Figure 25:
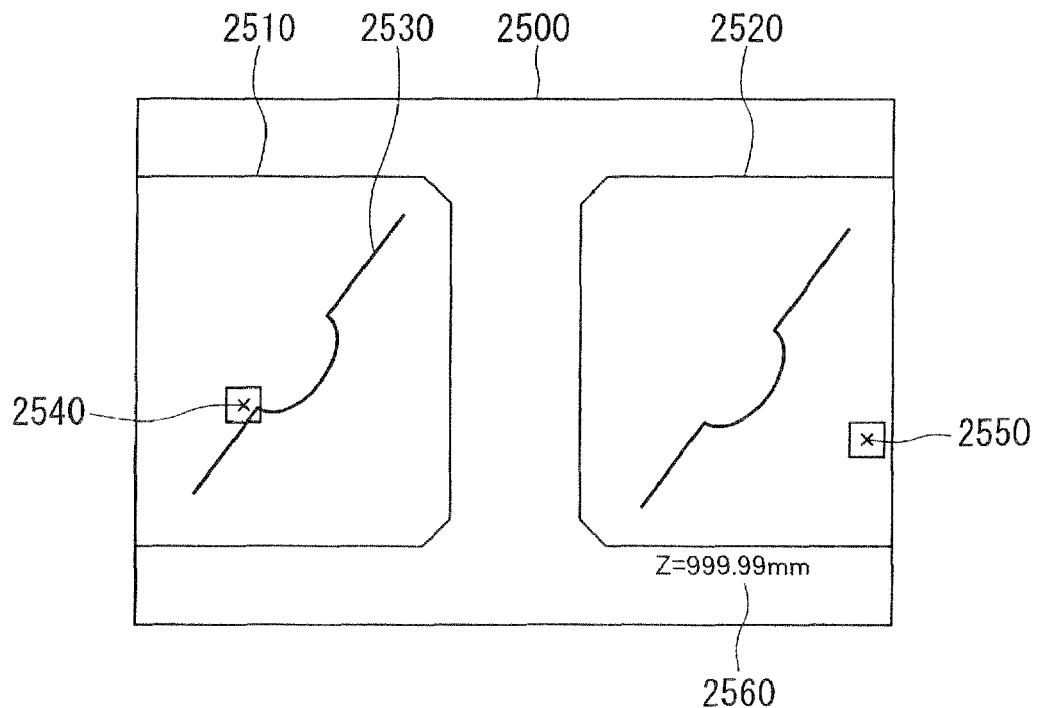
FIG. 25 is a reference view illustrating a display screen of a known measuring endoscope apparatus.

FIG. 23 shows measurement processing corresponding to FIGS. 12 and 20. The same processing as the processing shown in FIGS. 12 and 20 is denoted by the same reference numeral. FIG. 23 is different from FIGS. 12 and 20 in that processing of steps S1100 to S1150 is added. As shown in FIG. 23, first, the CPU 18 determines whether or not an instruction to move a pointer on a display screen has been input on the basis of a signal output from the operating portion 6 and input through the RS-232C I/F 17 (step S1100).

When the instruction to move the pointer is not input, the process proceeds to step S1150. In addition, when the instruction to move the pointer has been input, the CPU 18 performs processing for updating the display position of the pointer and calculates a contrast value of a texture (step S110). At this time, the CPU 18 calculates the contrast value of the texture from an image of the pattern area of 11×11 pixels around a measurement point set on the left image.

Then, the CPU 18 determines the contrast value of the texture (step S1120). In this determination, it is determined whether or not the image is suitable for the measurement (particularly the matching processing) by comparing the contrast value of the texture calculated in step S110 with a predetermined value. When the contrast value of the texture is the predetermined value or more, the process proceeds to step S1140. In addition, when the contrast value of the texture is less than the predetermined value, the image is not suitable for the measurement. Accordingly, in this case, the CPU 18 executes a control of displaying as a measurement result that the image is not suitable for the measurement (step S1130).

Subsequent to step S1120 or S1130, the CPU 18 determines whether or not the instruction to move the pointer on the display screen has been input (step S1140). The determination method is the same as that in step S1100. When the instruction to move the pointer has been input, the process returns to step S1110. In addition, when the instruction to move the pointer is not input, the CPU 18 determines whether or not an instruction to set a measurement point has been input on the basis of a signal output from the operating portion 6 and input through the RS-232C I/F 17 (step S1150). The instruction to set a measurement point also serves to instruct the start of actual measurement (particularly the matching processing). When the instruction to set the measurement point is not input, the process returns to step S1100. Moreover, when the instruction to set the measurement point has been input, the process proceeds to step S400. Subsequent processing is the same as described above.

In the above description, the matching reliability determination using the contrast value of the texture is performed until the instruction (instruction to start the measurement) to set a measurement point is input after the instruction to move the pointer is input. Accordingly, similar to the sixth operation example, it is possible to inform the user earlier that the reliability of matching processing is low. As a result, working efficiency can be improved. In addition, the user can recognize a location where the reliability of the matching processing is low in real time by operating the operating portion 6 to move the pointer.

As described above, according to the present embodiment working efficiency can be improved by executing a control according to a result of determination on the reliability of a measurement result. In particular, since the user can easily determine whether or not to end the measurement or whether or not to perform the measurement again by controlling the display form of a measurement result according to the result of determination on the reliability of the measurement result, working efficiency can be improved. In addition, since the reliability of a measurement result is improved by executing a control of changing to a modification mode in which the measurement position is modified when it is determined that the reliability of a measurement result is low, retrial of the measurement rarely occurs. As a result, working efficiency can be improved. In addition, since it is possible to inform the user earlier that the reliability of the matching processing is low by displaying a measurement result indicating the failure of the matching processing earlier than other things or by performing the matching reliability determination before the three-dimensional coordinate analysis processing, working efficiency can be improved.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. For example, although an example in which the optical adapter is of a replacement type has been described in the above embodiment, the optical adapter may not be of the replacement type, but may be fixed to the tip portion of the insertion portion.

The invention is not to be considered as being limited by the foregoing description, and is only limited by the scope of the appended claims.

According to the invention, an effect that working efficiency can be improved by executing a control according to a determination result on the reliability of a measurement result can be obtained. In particular, since the user can easily determine whether or not to end the measurement or whether or not to perform the measurement again by controlling the display form of a measurement result according to the determination result on the reliability of the measurement result, working efficiency can be improved. In addition, since the reliability of a measurement result is improved by executing a control of changing to a modification mode in which the measurement position is modified when it is determined that the reliability of a measurement result is low, retrial of the measurement rarely occurs. As a result, working efficiency can be improved.

What is claimed is:
1. A measuring endoscope apparatus comprising:
an endoscope that performs photoelectric conversion of a subject image to generate an imaging signal;
an imaging signal processing unit that processes the imaging signal to generate image data;
a measurement unit that executes measurement based on a principle of triangulation using the image data;

a display signal generating unit that generates a display signal for displaying a measurement result;

a determination unit that determines a reliability of the measurement result based on the image data;

a control unit that executes a control according to a determination result; and an input unit to which an instruction to move a pointer indicating a position of a measurement point on the subject image and an instruction to start the measurement are input;

wherein the display signal generating unit generates a display signal for displaying an image based on the image data, the measurement result, and the pointer;

wherein the determination unit determines the reliability of the measurement result at the position of the measurement point until the instruction to start the measurement is input to the input unit after the instruction to move the pointer is input to the input unit; and wherein the reliability of the measurement result is determinable by the determination unit in a state in which the pointer moves.

2. The measuring endoscope apparatus according to claim 1, wherein the control unit controls a display form of the measurement result according to the determination result.

3. The measuring endoscope apparatus according to claim 2, wherein the control unit controls the display form of the measurement result according to a value of a distance from a measurement position on a subject to an imaging surface of the endoscope.

4. The measuring endoscope apparatus according to claim 2, wherein the control unit controls the display form of the measurement result according to a value of a correlation function of a plurality of subject images regarding a same subject.

5. The measuring endoscope apparatus according to claim 2, wherein the control unit controls the display form of the measurement result according to a contrast value of a texture of a plurality of subject images regarding a same subject.

6. The measuring endoscope apparatus according to claim 2, wherein the control unit controls the display form of the measurement result according to a parallax of a corresponding point on another subject image corresponding to a measurement point on one subject image regarding a same subject from an epipolar line.

7. The measuring endoscope apparatus according to claim 1, wherein when it is determined that the reliability of the measurement result is low, the control unit executes a control of changing to a modification mode in which a corresponding point on another subject image corresponding to a measurement point on one subject image regarding a same subject is modified.

8. The measuring endoscope apparatus according to claim 1, wherein the measurement unit executes the measurement based on a measurement point on a first subject image and a corresponding point on a second subject image corresponding to the measurement point, and the control unit executes a control of displaying the measurement result earlier than displaying a region including the corresponding point when it is determined that the reliability of the measurement result is low.

9. The measuring endoscope apparatus according to claim 1, wherein the determination unit determines the reliability of the measurement result based on the image data before the measurement unit executes the measurement.

10. The measuring endoscope apparatus according to claim 1, wherein the determination unit determines the reliability of the measurement result based on the image data after the measurement unit executes the measurement.

11. The measuring endoscope apparatus according to claim 1, wherein the determination unit executes a first determination processing for determining the reliability of the measurement result based on the image data before the measurement unit executes the measurement, and executes a second determination processing for determining the reliability of the measurement result based on the image data after the measurement unit executes the measurement.

12. The measuring endoscope apparatus according to claim 1, wherein the control unit executes a control of displaying the determination result outside a measurable region on the image.

13. The measuring endoscope apparatus according to claim 1, wherein the reliability of the measurement result is determinable by the determination unit when the pointer is stopped.

14. The measuring endoscope apparatus according to claim 1, wherein a position of the measurement point is determinable by the control unit even if the reliability of the measurement result is low.

15. The measuring endoscope apparatus according to claim 1, wherein the control unit executes a control so as to switch whether or not the determination unit determines the reliability of the measurement result.

16. A non-transitory computer readable storage medium having a program stored thereon for causing a computer to perform functions comprising:

photoelectrically converting a subject image to generate an imaging signal;

processing the imaging signal to generate image data;

executing measurement based on a principle of triangulation using the image data;

generating a display signal for displaying a measurement result;

determining a reliability of the measurement result based on the image data;

executing a control according to a determination result; and accepting input of an instruction to move a pointer indicating a position of a measurement point on the subject image and an instruction to start the measurement, wherein a display signal is generated for displaying an image based on the image data, the measurement result, and the pointer, and wherein the reliability of the measurement result at the position of the measurement point is determined until the instruction to start the measurement is input after the instruction to move the pointer is input, and wherein the reliability of the measurement result is determinable in a state in which the pointer moves.

17. The non-transitory computer readable storage medium according to claim 16, wherein the measurement is executed based on a measurement point on a first subject image and a corresponding point on a second subject image corresponding to the measurement point, and a control of displaying the measurement result earlier than displaying a region including the corresponding point is executed when it is determined that the reliability of the measurement result is low.

18. The non-transitory computer readable storage medium according to claim 16, wherein the reliability of the measurement result is determined based on the image data before the measurement is executed.

19. The non-transitory computer readable storage medium according to claim 16, wherein the reliability of the measurement result is determined based on the image data after the measurement is executed.

20. The non-transitory computer readable storage medium according to claim 16, wherein a first determination processing for determining the reliability of the measurement result based on the image data is executed before the measurement is executed, and a second determination processing for determining the reliability of the measurement result based on the image data is executed after the measurement is executed.

21. The non-transitory computer readable storage medium according to claim 16, wherein a control is executed of displaying the determination result outside a measurable region on the image.

22. The non-transitory computer readable storage medium according to claim 16, wherein the reliability of the measurement result is determinable when the pointer is stopped.

23. The non-transitory computer readable storage medium according to claim 16, wherein a position of the measurement point is determinable even if the reliability of the measurement result is low.

24. The non-transitory computer readable storage medium according to claim 16, wherein the program is controllable so as to switch whether or not to determine the reliability of the measurement result.

* * * * *